United States Patent [19]

Breuer et al.

[11] Patent Number: 4,939,253

[45] Date of Patent: Jul. 3, 1990

[54] 2-OXOAZETIDIN-1-YLOXY ACETIC ACIDS AND ANALOGS

[75] Inventors: Hermann Breuer, Schoenhofen; Henner Straub, Regensburg, both of Fed. Rep. of Germany

[73] Assignee: E. R. Squibb & Sons, Inc., Princeton, N.J.

[21] Appl. No.: 515,727

[22] Filed: Jul. 21, 1983

Related U.S. Application Data

[63] Continuation-in-part of Ser. No. 404,945, Aug. 4, 1982, abandoned.

[51] Int. Cl.⁵ ................. C07D 205/08; C07D 417/12; A61K 31/395; A61K 31/425
[52] U.S. Cl. .................................................. 540/355
[58] Field of Search .................. 260/245.4, 239 A; 540/355

[56] References Cited

FOREIGN PATENT DOCUMENTS 3328047 2/1984 Fed. Rep. of Germany .

OTHER PUBLICATIONS

Woulfe, Tet. Letters 25, 3293-6 (1984).
Moulin et al, Chem. Abs 80, 70691(b) 1973.
Weigele et al, J. Organic Chem 41, 390 (1976).

*Primary Examiner*—Mark L. Berch
*Attorney, Agent, or Firm*—Donald J. Barrack; Stephen Venetianer

[57] ABSTRACT

Antibiotic activity is exhibited by β-lactams having an

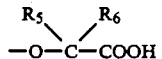

substituent (and analogs thereof) in the 1-position and an acylamino substituent in the 3-position.

25 Claims, No Drawings

2-OXOAZETIDIN-1-YLOXY ACETIC ACIDS AND ANALOGS

This is a continuation-in-part of U.S. patent application Ser. No. 404,945, filed Aug. 4, 1982, abandoned.

BACKGROUND OF THE INVENTION

The β-lactam ring,

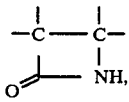

has been known since the late nineteenth century. While knowledge of β-lactam chemistry developed during the early 1900's, it was not until 1929 that Fleming reported in *Brit. J. Exper. Pathol.* 10, 226 (1929) that a fermentation product of the organism *Penicillium notatum* had antibiotic properties. The compound which Fleming had worked with was benzylpenicillin.

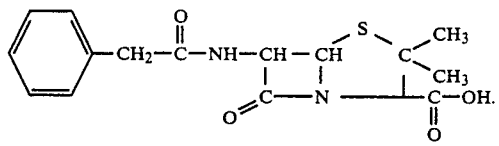

The in vivo activity of benzylpencillin against various bacteria was reported by Chain et al. in *Lancet*, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid.

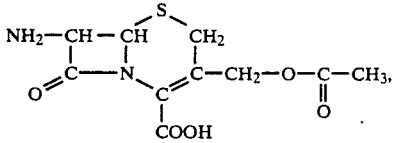

This patent was followed by U.S. Pat. No. 2,951,839, issued Sept. 6, 1960, also to Doyle et al., which discloses the use of 6-amino-penicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalsporin C,

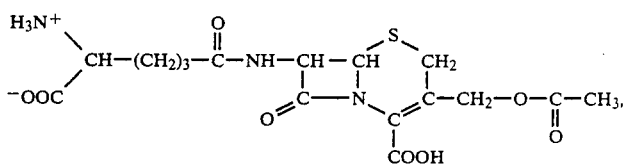

proved to be an important stepping stone in cephalosporin research. Removal of the acyl group in the 7-position of cephalosporin C yields 7-aminocephalosporanic acid,

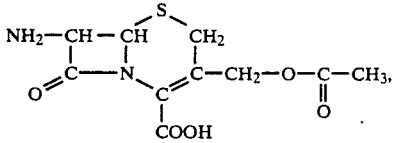

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

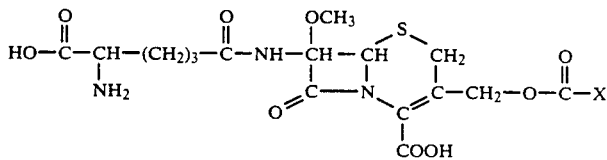

cephamycin B: 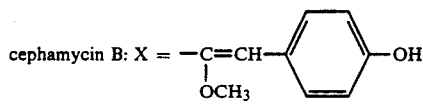

cephamycin C: X = —NH₂.

Stapley et al. reported that cephamycin A and cephamycin B each exhibits a similar range of potencies against gram-negative and gram-positve bacteria and cephamycin C had greater potency against gram-negative bacteria than against gram-positive bacteria. Cephamycin C was reported to be the most active of the three antibiotics.

Scannell et al., *The Journal of Antibiotics*, XXVIII(1):1 (1975), disclose the isolation from a fermentation broth of Streptomyces species 372A of (S)-alanyl-3-[α-(S)-chloro 3-(S) hydroxy-2-oxo-3-azetldinyl-methyl]-(S)-alanine, which has the formula

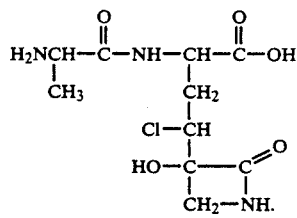

The structure of the above naturally occurring monocyclic β-lactam containing molecule is similar to the structure of the earlier discovered β-lactam containing molecules known as tabotoxins, i.e.,

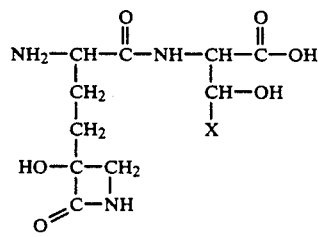

wherein X is hydrogen or methyl as reported by Stewart, *Nature*, 229:174 (1974), and Taylor, et al., *Biochem. Biophys. Acta.*, 286:107 (1972).

Recently, several novel series of naturally occurring β-lactam antibiotics have been isolated. The nocardicins, nocardicin A and B, are monocyclic β-lactams having the formula

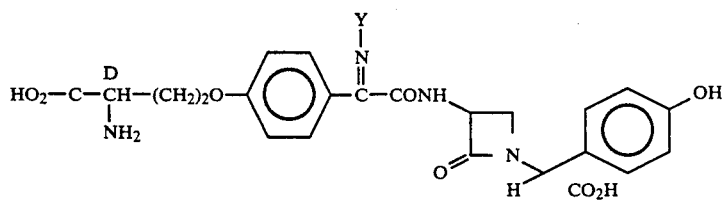

nocardicin A: Y=-syn(Z)OH
    nocardicin B: Y=-anti(E)OH, as reported by Hashimoto et al., *The Journal of Antibiotics*, XXIX (9):890 (1976).

Clavulanic acid, a bicyclic β-lactam antibiotic isolated from fermentation broths of *Streptomyces clavuligerus*, has the formula

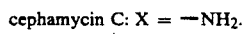

i.e., Z-(2R,5R)-3-(β-hydroxyethylidene)-7-oxo-4-oxa-1-azabicyclo[3,2,0]heptane-2 carboxylic acid, as reported by Lloyd et al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers Schonberg et al., *J.A.C.S.*, 100:20, 6491 (1978), thienamycin has the structure

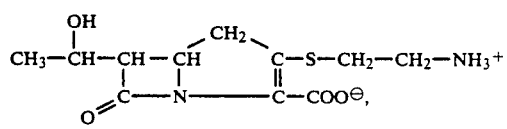

Additional fused β-lactams, olivanic acid derivatives, have recently been isolated from cultures of *Streptomyces olivaceus*. As disclosed by Brown et al., *J.C.S. Chem. Comm.*, these olivanic acid derivatives have the formulas

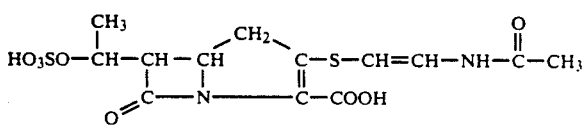

and

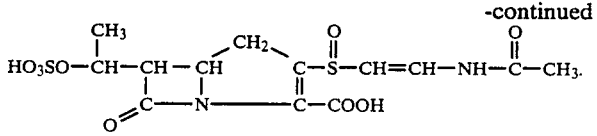

The isolation of the above antibiotics, and a discussion of their activity, is reported by Butterworth et al., *The Journal of Antibiotics*, XXXII(4):294 (1979) and by Hood et al., *The Journal of Antibiotics*, XXXII(4):295 (1979).

Another recently isolated β-lactam antibiotic is PS-5, reported by Okamura et al., *The Journal of Antibiotics*, XXXI: 480 (1978) and *The Journal of Antbiotics*, XXXII(4):262 (1979). The structure of this antibiotic, which is produced by *Streptomyces cremeus* subspecies *auratilis*, is reported to be

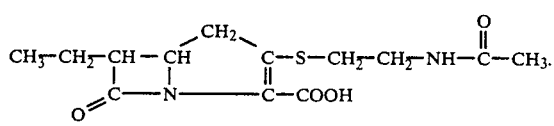

Structurally related antibiotics PS-6 and PS-7 are reported in European Patent application serial no. 1,567 to have the respective structures

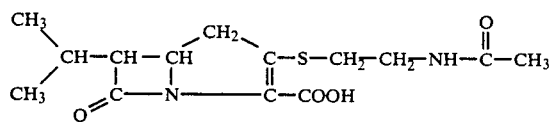

and

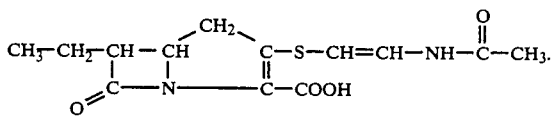

Two recently disclosed series of β-lactam antibiotics are the monocyclic β-lactams having the formulas

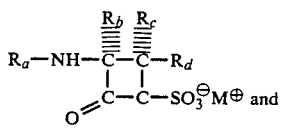

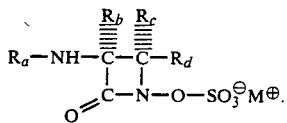

wherein $R_a$ is acyl, $R_b$ is hydrogen or alkoxy, $R_c$ and $R_d$ are various organic substituents, and $M^\oplus$ is a cation. The antibiotics having an $-SO^\ominus M^\oplus$ activating qroup are disclosed in United Kingdom patent application No. 2,071,650, published Sept. 23, 1981. The antibiotics having an $-O-SO^\ominus M^\oplus$ activating group are disclosed in European patent application No. 0051381, published May 12, 1982, and U.S. Pat. No. 4,337,197, issued June 29, 1982.

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a substituent having the formula

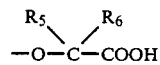

(or an ester or salt thereof) attached to the nitrogen atom in the nucleus.

β-Lactams having a

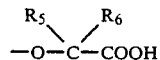

substituent (or ester or salt thereof) in the 1-position and an acylamino substituent in the 3-position exhibit activity against a range of gram negative and gram-positive bacteria.

Illustrative members of the novel family of β-lactam antibiotics of this invention are those encompassed by the formula

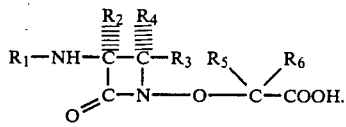

I and esters and salts thereof.

As used in formula I, and throughout the specification, the symbols are as defined below.

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle (referred to hereinafter as $R_x$) or one of $R_3$ and $R_4$ is hydrogen and the other is azido, halomethyl, dihalomethyl, trihalomethyl, alkoxycarbonyl, 2-phenyletheny, 2-phenylethynyl, carboxyl, $-CH_2X_1$ [wherein $X_1$ is azido, amino ($-NH_2$), hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

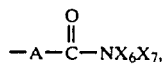

$-S-X_2$, or $-O-X_2$ (wherein A, $X_2$, $X_6$ and $X_7$ are as hereinafter defined)], $-S-X_2$ or $-O-X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

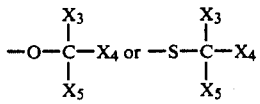

[wherein one of X₃ and X₄ is hydrogen and the other is hydrogen or alkyl, or X₃ and X₄ when taken together with the carbon atom to which they are attached form a cycloalkyl group; and X₅ is formyl, alkanoyl, phenylcarbonyl, (substituted phenyl)carbonyl, phenylalkylcarbonyl, (substituted phenyl)alkyl- carbonyl, carboxyl, alkoxycarbonyl, aminocarbonyl

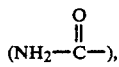

substituted amino)-carbonyl, or cyano (—C≡N)], or

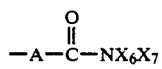

(wherein A is —CH=CH—, —(CH₂)ₙ—, —CH₂—O—, —CH₂—NH—, or —CH₂—S—CH₂—, n is 0, 1 or 2, and X₆ and X₇ are the same or different and each is hydrogen, alkyl, phenyl or substituted phenyl, or X₆ is hydrogen and X₇ is amino, substituted amino, acylamino or alkoxy, or X₆ and X₇ when taken together with the nitrogen atom to which they are attached form a 4, 5, 6 or 7-membered heterocycle); and R₅ and R₆ are the same or different and each is hydrogen, alkyl, alkenyl, alkynyl, phenyl, substituted phenyl, cycloalkyl or R_x, or R₅ and R₆ together with the carbon atom to which they are attached are cycloalkyl or R_x, or one of R₅ and R₆ is hydrogen and the other is azido, halomethyl, dihalomethyl, trihalomethyl, halogen, alkoxycarbonyl, alkenyl, alkynyl, 2-phenylethenyl, 2-phenylethynyl, carboxyl, —CH₂—X₁, —S—X₂, —O—X₂, or

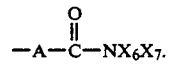

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—NH₂), halogen, hydroxy, carboxy, cyano, alkoxycarbonyl, aminocarbonyl, alkanoyloxy, alkoxy, phenyloxy, (substituted phenyl)oxy, R_x-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), or carboxyl groups.

The expression "a 4,5,6 or 7-membered heterocycle" (referred to as "R_x") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

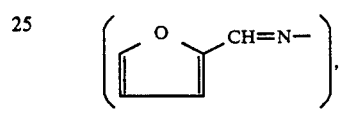

benzylideneimino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3,-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7 membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3 phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1- hexahydroazepinyl, 2-oxo-3-pyrrolidinyl, 2-oxo-3-tetrahydrofuranyl, 2,3-dioxo- 1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NY₁Y₂ wherein Y₁ is hydrogen, alkyl, phenyl, substituted phenyl, phenylalkyl or (substituted phenyl)alkyl, and Y₂ is alkyl, phenyl, substituted phenyl, phenylalkyl, (substituted phenyl)alkyl, hydroxy, cyano, alkoxy, phenylalkoxy, or amino (—NH₂).

The term "acyl" refers to all organic radicals derived from an organc acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see for example, *Cephalosporins and Penicillins*, edited by Flynn, Academic Press (1972), German Offenlegungsschrift No. 2,716,677, published Oct. 10, 1978, Belgian patent No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexdienyl; or alkyl or alkenyl substituted with one or more halogen, cyano, nitro, amino, mercapto, alkylthio, or cyanomethylthio groups.

(b) Carbocyclic aromatic groups having the formula

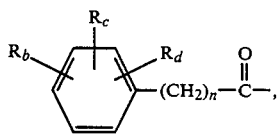

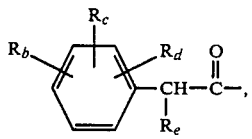

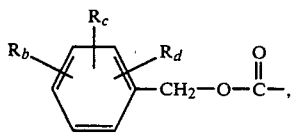

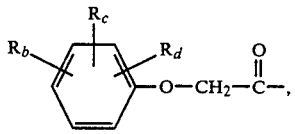

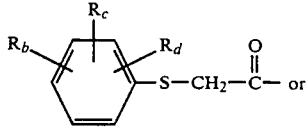 or

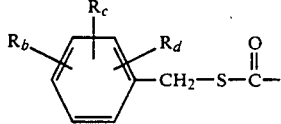

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkkylhydrazino, phenylhydrazino, or thio.

Preferred carbocyclic aromatic acyl groups include those having the formula

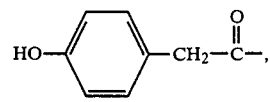

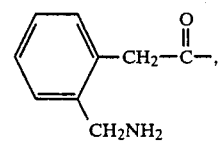

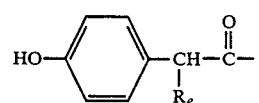

($R_e$ is preferably a carboxyl salt or sulfo salt) and

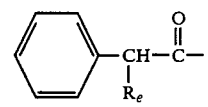

($R_e$ is preferably a carboxyl salt or sulfo salt).

(c) Heteroaromatic groups having the formula

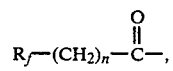

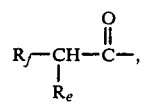

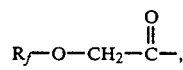

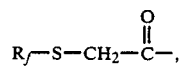

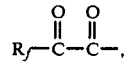

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

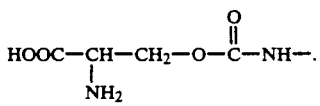

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6 aminopyridin-2-yl.

(d) [[(4-Substituted-2,3-dioxo-1-piperazinyl)carbonyl]amino]arylacetyl groups having the formula

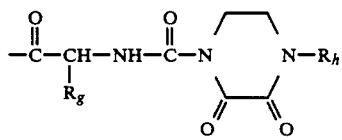

wherein $R_g$ is an aromatic group (including carbocyclic aromatics such as those of the formula

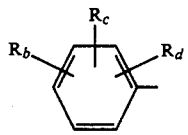

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

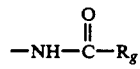

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

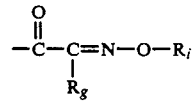

wherein $R_g$ is as defined above and $R_i$ is hydrogen, alkyl, cycloalkyl, alkylaminocarbonyl, arylaminocarbonyl (i.e.,

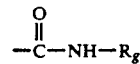

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts and prodrug esters thereof), amido, alkoxycaronyl, phenylmethoxycarbonyl, diphenylmethoxycarbonyl, hydroxyalkoxyphosphinyl, dihydroxyphosphinyl, hydroxy(phenylmethoxy)phosphinyl, or diakoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1 carboxy-1-methylethyl, 2,2,2-trifluoroethyl or 1-carboxycyclopropyl.

(f) (Acylamino)arylacetyl groups having the formula

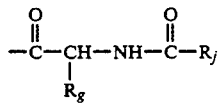

wherein $R_g$ is a defined above and $R_j$ is

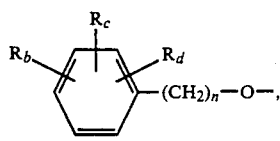

amino, alkylamino, (cyanoalkyl)-amino, amido, alkylamido, (cyanoalkkyl)amido,

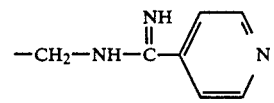

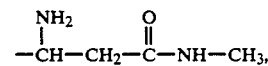

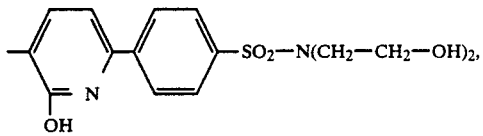

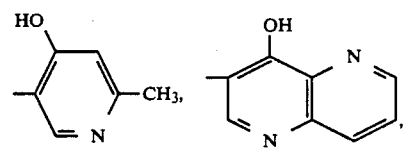

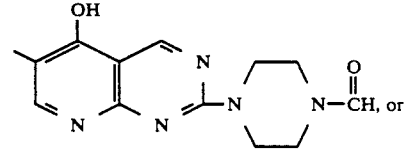

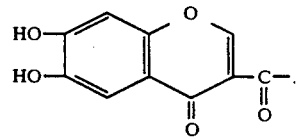

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

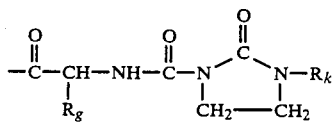

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases. e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

As set forth throughout the specification, β-lactams having in the 1-position an ester of the group

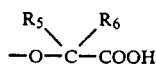

are contemplated as an integral part of this invention. Exemplary esters include alkyl, alkenyl, alkynyl, cycloalkyl, (cycloalkyl)-alkyl, $R_x$-alkyl, trialkylsilylalkyl, mono-, di- or trihaloalkyl, hydroxyalkyl, alkoxyalkyl, carboxyalkyl, alkoxycarbonylalkyl, diphenylmethoxycarbonylalkyl, carbamoylalkyl, alkylcarbamoylalkyl, dialkylcarbamoylalkyl, indanyl, phenyl, substituted phenyl, phenylalkyl, (substituted phenyl)alkyl, $R_x$-carbonylalkyl,

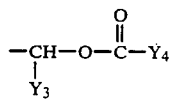

wherein $Y_3$ is hydrogen, alkyl or phenyl and $Y_4$ is hydrogen, alkyl, cycloalkyl, (cycloalkyl)oxy, phenyl, or alkoxy, or together $Y_3$ and $Y_4$ are —(CH$_2$)$_2$—, —(CH$_2$)$_3$—, —CH=CH—, or

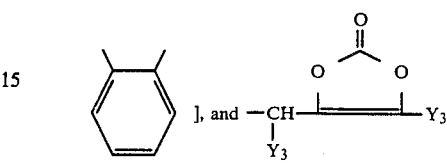

esters.

Hydrolyzable esters are those esters that can be hydrolyzed in vivo to give the parent carboxylic acid product; they exhibit the antibiotic activity of the parent carboxylic acid. Non-hydrolyzable esters (esters that do not hydrolze in vivo to the parent carboxylic acid) are contemplated for use in this invention as intermediates; some of them are also active as antibiotics.

β-Lactams having a

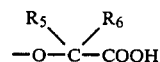

substituent (or an ester or salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins, (e.g., cephamycin C).

With respect to the preferred β-lactams of formula I, the structural formulas have been drawn to show the stereochemistry at the chiral center in the 3-position. Because of the nomenclature convention, those compounds of formula I wherein $R_2$ is hydrogen have the S configuration and those compounds of formula I wherein $R_2$ is methoxy have the R configuration.

Also included within the scope of this invention are racemic mixtures which contain the above-described β-lactams.

DETAILED DESCRIPTION OF THE INVENTION

β-Lactams having a

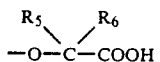

subtitutent (or an ester or salt thereof) in the 1-position of the β-lactam nucleus and an acylamino substituent in the 3-position of the β-lactam nucleus have activity against a range of gram-negative and gram-positive organisms. The

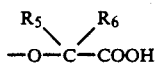

substituent (or an ester or salt thereof) is essential to the activity of the compounds of this invention.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactams of this invention can be prepared from an amino acid having the formula

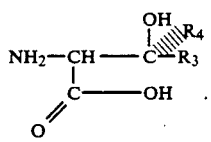

The amino group is first protected with a classical protecting group (e.g., t-butoxycarbonyl, benzyloxycarbonyl, o-nitrophenylsulfenyl, etc.), yielding a compound having the formula

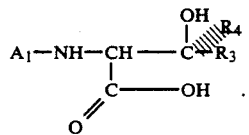

In formula III, and throughout the specification, the symbol "$A_1$" refers to a nitrogen protecting group. For certain products of formula I, the desired acyl group "$R_1$" can be used as the protecting group "$A_1$" and thus incorporated at the beginning of the reaction sequence.

The carboxyl group of a protected amino acid of formula III is then reacted with an amine having the formula

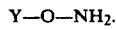

In formula IV, and throughout the specification, the symbol "Y" refers to benzyl, trityl, pivaloyl, —CH$_2$CH(NHA$_2$)CO$_2$ alkyl, t-butyl, p-nitrobenzyl, benzhydryl, 2-cyanoethyl, 2-trimethylsilylethyl, trichloroethyl, p-anisyl, inter alia (wherein the symbol "$A_2$" refers to a nitrogen protecting group). The reaction proceeds in the presence of a coupling agent such as 1-ethyl-3-(3-dimethylaminopropyl)carbodiimide or dicyclohexylcarbodiimide, and yields a compound having the formula

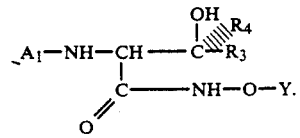

The hydroxyl group of a compound of formula V is converted to a leaving group, using, for example, a classical reagent such as methanesulfonyl chloride (methanesulfonyl is referred to hereinafter as "Ms").

The fully protected compound having the formula

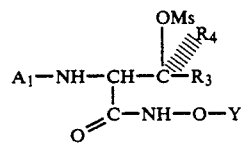

is cyclized by treatment with base, e.g., potassium carbonate. The reaction is preferably carried out in an organic solvent such as acetone, under reflux conditions, and yields a compound having the formula

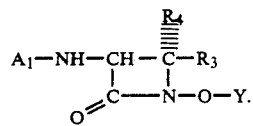

Alternatively, cyclization of a compound of formula V can be accomplished without first converting the hydroxyl group to a leaving group. Treatment of a compound of formula V with triphenylphosphine and diethylazodicarboxylate or carbon tetrachloride, yields a compound of formula VII.

Both of the methods disclosed above for ring closure of a compound of, formula V result in the inversion of the stereochemistry of the $R_3$ and $R_4$ substituents.

Selective reduction of a compound of formula VII (using catalytic hydrogenation if Y is benzyl or by treatment with a base such as sodium sulfide or sodium hydroxide if Y is pivaloyl or with DBU if Y is —CH$_2$CH(NHA$_2$)CO$_2$alkyl yields the corresponding compound having the formula

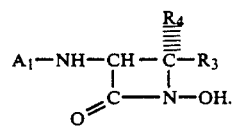

Alkylation of a hydroxamic acid of formula VIII with an activated and protected (if needed) form of a compound having the formula

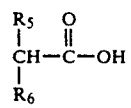

can be accomplished by first generating the anion of the hydroxamic acid with a suitable base, and then reacting the resulting compound with an activated form of an acetic acid derivative of formula IX. Activated and protected forms of compounds of formula IX have the formula $$Y_5-\underset{\underset{R_6}{|}}{\overset{\overset{R_5}{|}}{C}}-\overset{\overset{O}{\|}}{C}-OY_6, \quad \text{IXa}$$

wherein $Y_5$ is a suitable leaving group, such as a halogen atom (preferably bromine or chlorine), a mesylate or triflate group, or any one of the other leaving groups well known in the art, and $Y_6$ is hydrogen or an ester group. The above alkylation procedure has been described as a two step sequence, but both steps can be performed simultaneously. The resulting product has the formula $$A_1-NH-CH-\overset{\overset{R_4}{\equiv}}{C}-R_3 \quad R_5 \quad R_6 \atop \underset{O}{\overset{}{\diagdown}}\overset{}{C}-N-O-C-C-OY_6. \quad X$$

Deprotection of the 3-amino substituent of a compound of formula X can be accomplished using art-recognized techniques. If, for example, the protecting group is t-butoxycarbonyl, trifluoroacetic acid can be used to deprotect the amino group. If the protecting group is benzyloxycarbonyl, catalytic (e.g., palladium on charcoal) hydrogenation can be used. If the protecting qroup is o-nitrophenylsulfenyl, p-toluenesulfonic acid can be used in combination with p-thiocresol. The deprotected compound has the formula $$NH_2-CH-\overset{\overset{R_4}{\equiv}}{C}-R_3 \quad R_5 \quad R_6 \atop \underset{O}{\overset{}{\diagdown}}\overset{}{C}-N-O-C-C-OY_6. \quad XI$$

and is a key intermediate for preparing the compounds of this invention. The compounds of formula XI form an integral part of this invention.

Well known acylation techniques can be used to convert a compound of formula XI to the corresponding compound having the formula $$R_1-NH-CH-\overset{\overset{R_4}{\equiv}}{C}-R_3 \quad R_5 \quad R_6 \atop \underset{O}{\overset{}{\diagdown}}\overset{}{C}-N-O-C-C-OY_6. \quad XII$$

Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or N-hydroxysuccinimide. In those instances wherein the acyl group ($R_1$) contains reactive functionality (such as amino or carboxyl groups) it may be necessary to first protect these functional groups, then carry out the acylation reaction, and finally deprotect the resulting product.

Deprotection of the carboxylic acid group, followed by esterification (if desired), yields the desired products of formula I wherein $R_2$ is hydrogen. Esterification procedures are illustrated in the examples.

Alternative means are available for converting an intermediate of formula X to a product of formula I. For example, a compound of formula X can be reacted with N-methyl-N-trimethylsilyl-trifluoroacetamide (MSTFA) and a silane such as iodotrimethylsilane to cleave the "$A_1$" and "$Y_6$" groups and yield the corresponding 3-trimethylsilylamino compound, which can be acylated using the above-described procedures.

The products of formula I wherein $R_2$ is methoxy can be prepared from the corresponding compound of formula VII. Halogenating (preferably chlorinating) the amide nitrogen of a compound of formula VII yields a compound having the formula $$A_1-\underset{\underset{O}{\overset{}{\diagdown}}\overset{}{C}-N-O-Y.}{\overset{\overset{Cl}{|}}{N}-CH-\overset{\overset{R_4}{\equiv}}{C}-R_3} \quad XIII$$

Reagents and procedures of N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XIII with a methoxylating agent, e.g., an alkali metal methoxide, yields a compound (in combination with its enantiomer if $R_3$ and $R_4$ are the same or if XIII is a racemic mixture) having the formula $$A_1-NH-\overset{\overset{OCH_3}{\equiv}}{\underset{\underset{O}{\overset{}{\diagdown}}\overset{}{C}-N-O-Y.}{C}}-\overset{\overset{R_4}{\equiv}}{C}-R_3 \quad XIV$$

The reaction can be run in an organic solvent, e.g., a polar organic solvent such as tetrahydrofuran, at a reduced temperature.

Alternatively, a compound of formula VII can be converted to a compound of formula XIV using a single step procedure. The methoxylating agent can first be mixed with a compound of formula VII and the N-chlorinating reagent then added to the reaction mixture.

Conversion of a compound of formula XIV to the desired products of formula I (or an ester thereof) can be accomplished using the procedures described above for the conversion of an intermediate of formula XIV to a product of this invention.

An alternative route for the preparation of the compounds of this invention comprises a more direct synthesis of the compounds of formula X. Reaction of an N-protected amino acid of formula III with a compound, formed by reaction of a compound of formula IXa with N-hydroxyphthalimide followed by reaction with hydrazine, yields a compound having the formula

XV

[Structure: A₁—NH—CH(—C(OH)(R₄)(R₃))—C(=O)—NH—O—C(R₅)—C(R₆)(=O)—OY₆]

Following the procedures described above, the hydroxyl group of a compound of formula XV can be converted to a leaving group and the resulting compound cyclized to yield the corresponding compound of formula X.

The starting materials of formula II are readily obtainable using art-recognized procedures; see, for example *Synthesis*, pg. 216 (1979) and *J. Org. Chem.*, 44:3967 (1979).

The following tables set forth compounds of this invention which have been prepared utilizing the methodology described above. The methodology is further illustrated with respect to specific compounds in the examples that follow the tables. In the compounds set foth in these tables, the oxime stereochemistry is syn.

TABLE I

[Structure of compound with R_x substituent, terminating in O—CH₂—C(=O)—O⁻K⁺]

| R_x |
|---|
| CH₃ |
| CH₂CH₃ |
| CH(CH₃)₂ |
| CH₂CF₃ |
| CH₂C(=O)—NH₂ |
| CH₂CO₂⁻K⁺ |
| CH₂CO₂CH₃ |
| C(CH₃)₂CO₂⁻K⁺ |
| C(CH₃)₂CO₂CH₃ |
| C(CH₃)₂C(=O)—NH₂ |
| C(CH₃)₂CO₂CH(phenyl)₂ |

TABLE II

[Structure of compound with R_y substituent, terminating in O—CH₂—C(=O)—O—R_y]

| R_y |
|---|
| CH₃ |
| CH₂CH₃ |

TABLE II-continued

[Same structure as Table II]

| R_y |
|---|
| CH(CH₃)₂ |
| C(CH₃)₃ |
| CH₂CH₂CH₃ |
| CH₂=CHCH₃ |
| CH₂—phenyl |
| CH₂—C(=O)—O—C(CH₃)₃ |
| CH₂—indanyl |
| CH₂C≡CH |
| CH(CH₂CH₃)₂ |
| tetrahydrothiophenyl |
| thiacyclohexyl |
| CH₂CH(CH₃)₂ |
| CH₂C(CH₃)₃ |
| CH₂CH(CH₂CH₃)₂ |
| CH₂—tetrahydrothiophenyl |

| R_y |
|---|
| CH₂—phenyl |
| CH₂CF₃ |
| CH₂—pyridyl |
| CH₂CH₂Cl |
| CH₂CH₂OH |
| CH₂CH₂OCH₃ |
| CH₂CH₂Si(CH₃)₃ |
| CH₂CH₂—imidazolyl |

TABLE II-continued

[Structure: thiazole-containing β-lactam with N—O—CH$_2$—C(O)—O—R$_y$, OCH$_3$ on oxime]

| R$_y$ |
|---|
| phenyl (C$_6$H$_5$) |
| CH$_2$—O—CH$_3$ |
| CH$_2$—O—C(O)—CH$_3$ |
| CH(CH$_3$)—O—C(O)—CH$_3$ |
| CH$_2$—O—C(O)—C(CH$_3$)$_3$ |
| CH(CH$_3$)—O—C(O)—O—CH$_2$CH$_3$ |
| CH(CH$_3$)—O—C(O)—O—cyclopentyl |
| (5-methyl-2-oxo-1,3-dioxol-4-yl)methyl |
| CH$_2$—C(O)—CH$_3$ |
| CH(CH$_3$)—C(O)—O—CH$_3$ |
| CH$_2$—C(O)—O—CH(CH$_3$)$_2$ |
| CH$_2$—C(O)—O—CH$_2$CH$_3$ |
| CH$_2$—C(O)—O—CH(CH$_2$CH$_3$)$_2$ |
| CH$_2$—C(O)—O—CH(C$_6$H$_5$)$_2$ |
| CH$_2$—C(O)—O$^{\ominus}$Na$^{\oplus}$ |
| CH$_2$—C(O)—NH—CH(CH$_3$)$_2$ |

TABLE II-continued

[Same structure as above]

| R$_y$ |
|---|
| CH$_2$—C(O)—NH—C(CH$_3$)$_3$ |
| CH$_2$—C(O)—N(morpholino) |
| CH$_2$—C(O)—NH$_2$ |
| CH$_2$—C(O)—O—CH(CH$_2$CH$_2$CH$_3$)$_2$ |
| CH(CH$_3$)—C(O)—O—CH(CH$_2$CH$_3$)$_2$ |

TABLE III

[Structure: thiazole-containing β-lactam with O—CH$_2$CH$_3$ on oxime, N—O—CH$_2$—C(O)—O—R$_y$]

| R$_y$ |
|---|
| potassium salt |
| CH$_3$ |
| CH(CH$_3$)$_2$ |
| CH(CH$_2$CH$_3$)$_2$ |

TABLE IV

[Structure: thiazole-containing β-lactam with oxime —O—C(CH$_3$)$_2$—C(O)—O—R$_z$, and N—O—CH$_2$—C(O)—O—R$_y$]

| R$_z$ | R$_y$ |
|---|---|
| K | K |
| CH$_3$ | CH$_3$ |
| CH$_2$CH$_3$ | CH$_3$ |
| CH(CH$_3$)$_2$ | CH$_3$ |
| CH$_2$CH$_2$CH$_3$ | CH$_3$ |
| CH$_2$CH=CH$_2$ | CH$_3$ |
| CH$_2$—C$_6$H$_5$ | CH$_3$ |

TABLE IV-continued

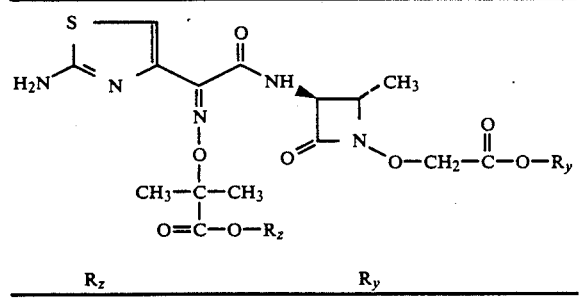

| $R_z$ | $R_y$ |
|---|---|
| CH$_2$—C(=O)—O—C(CH$_3$)$_3$ | CH$_3$ |
| CH$_3$ | CH(CH$_3$)$_2$ |
| CH$_2$CH$_3$ | CH(CH$_3$)$_2$ |
| CH(CH$_3$)$_2$ | CH(CH$_3$)$_2$ |
| CH$_2$CH$_2$CH$_3$ | CH(CH$_3$)$_2$ |
| CH$_2$CH$_2$CH=CH$_2$ | CH(CH$_3$)$_2$ |
| CH$_2$C≡CH | CH(CH$_3$)$_2$ |
| CH$_2$—Ph | CH(CH$_3$)$_2$ |
| CH(Ph)$_2$ | CH(CH$_3$)$_2$ |
| CH$_2$—C(=O)—O—C(CH$_3$)$_3$ | CH(CH$_3$)$_2$ |
| (4-methyl-1,3-dioxol-2-one-5-yl-methyl) | CH(CH$_3$)$_2$ |
| CH$_3$ | CH(CH$_2$CH$_3$)$_2$ |
| CH$_2$CH$_3$ | CH(CH$_2$CH$_3$)$_2$ |
| CH(CH$_3$)$_2$ | CH(CH$_2$CH$_3$)$_2$ |
| CH$_2$CH$_2$CH$_3$ | CH(CH$_2$CH$_3$)$_2$ |
| CH$_2$CH=CH$_2$ | CH(CH$_2$CH$_3$)$_2$ |
| CH$_2$C≡CH | CH(CH$_2$CH$_3$)$_2$ |
| CH$_2$—Ph | CH(CH$_2$CH$_3$)$_2$ |
| CH(Ph)$_2$ | CH(CH$_2$CH$_3$)$_2$ |
| CH$_2$—C(=O)—O—C(CH$_3$)$_2$ | CH(CH$_2$CH$_3$)$_2$ |
| (4-methyl-1,3-dioxol-2-one-5-yl-methyl) | CH(CH$_2$CH$_3$)$_2$ |

TABLE V

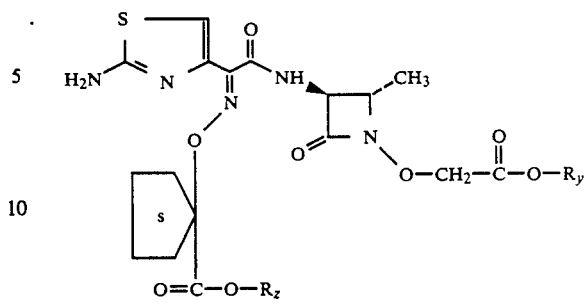

| $R_z$ | $R_y$ |
|---|---|
| potassium salt | potassium salt |
| CH$_3$ | CH(CH$_3$)$_2$ |
|  | CH(CH$_3$)$_2$ |
| CH(Ph)$_2$ | CH(CH$_3$)$_2$ |
| CH$_2$—C(=O)—O—C(CH$_3$) | CH(CH$_3$)$_2$ |
| CH$_3$ | CH(CH$_2$CH$_3$)$_2$ |
|  | CH(CH$_2$CH$_3$)$_2$ |
| CH(Ph)$_2$ | CH(CH$_2$CH$_3$)$_2$ |
| CH$_2$—C(=O)—O—C(CH$_3$)$_3$ | CH(CH$_2$CH$_3$)$_2$ |
| CH$_2$—C(=O)—O—C(CH$_3$)$_3$ | CH$_2$—C(=O)—O—C(CH$_3$)$_3$ |

TABLE VI

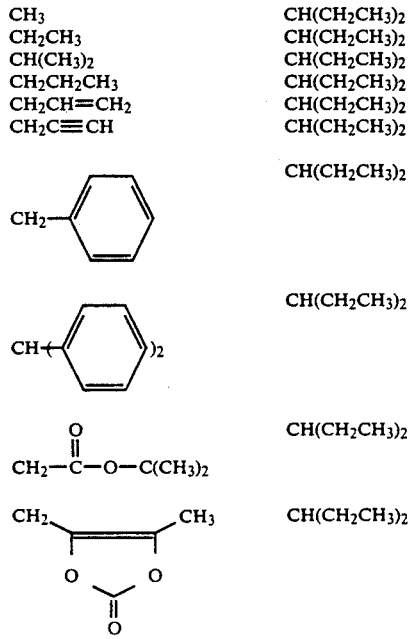

$R_w$

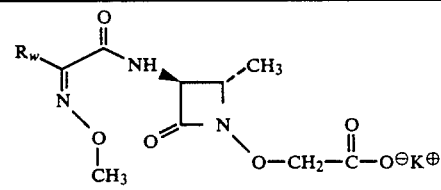

TABLE VII

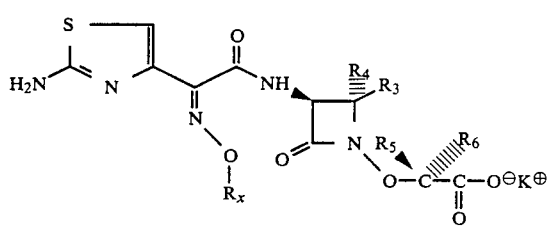

| R3 | R4 | R5 | R6 | Rx |
|---|---|---|---|---|
| H | CH3 | H | H | CH3 |
| H | CH3 | CH3 | CH3 | CH3 |
| H | CH3 | CH3 | H | CH3 |
| H | CH3 | (H, CH3) | | CH3 (diastereomeric mixture) |
| H | CH3 | H | CH3 | CH3 |
| H | CH3 | H | H | C(CH3)2—CO2⊖K⊕ |
| H | CH3 | H | C2H5 | C(CH3)2—CO2⊖K⊕ |
| H | CH3 | C2H5 | H | C(CH3)2—CO2⊖K⊕ |
| H | CH3 | (H, C2H5) | | C(CH3)2—CO2⊖K⊕ (diastereomeric mixture) |
| H | H | CH3 | CH3 | CH3 |

TABLE VIII

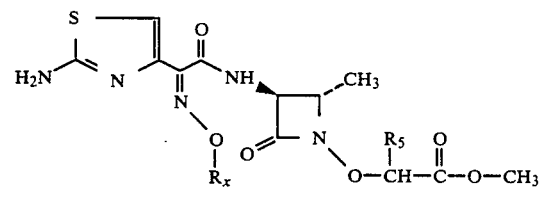

| Rx | R5 |
|---|---|
| CH2CO2⊖Na⊕ | H |
| CH2—C(=O)—NH2 | H |
| C(CH3)2CO2H | H |
| CH3 | CH3 |

TABLE IX

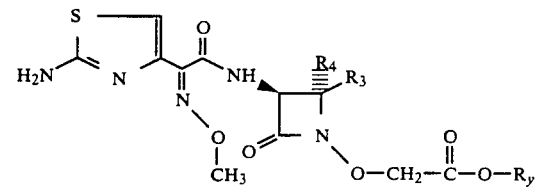

| R3 | R4 | Ry |
|---|---|---|
| CH3 | H | potassium salt |
| H | CH2CH3 | potassium salt |
| H | CH(CH3)2 | potassium salt |
| H | CH2CH2CH3 | potassium salt |
| H | CH2N3 | potassium salt |
| H | CH2—O—CH3 | CH3 |

TABLE X

[structure as shown with R5 and Rx substituents]

| R5 | Rx |
|---|---|
| F | CH3 |
| H | C(CH3)2—CO2⊖K⊕ |
| F | C(CH3)2—CO2⊖K⊕ |

EXAMPLE 1

[3S(Z)]-[[3-[[(2-Amino-4-thiazolyl)(methoxyimino)-acetyl]amino]-2-oxo-1-azetidinyl]oxy]acetic acid 1,1-dimethylethyl ester (A)

O-(t-Butyloxycarbonylmethyl)-α-N-(benzyloxycarbonyl)-L-serine hydroxamate

A solution of dicyclohexylcarbodiimide (57.5 g, 0.28 mol) in dry tetrahydrofuran (60 ml) was dropped into a solution of N-α-(benzyloxycarbonyl)-L-serine (66.9 g, 0.28 mol), 1-hydroxybenzotriazole hydrate (42.0 g, 0.28 mol) and t-butylaminoxyacetate (41.2 g. 0.28 mol) in dry tetrahydrofuran (1.4 L) at 0°-5° C. The mixture was stirred overnight at room temperature. The precipitate (dicyclohexylurea) was removed by filtration and the filtrate evaporated in vacuo. The residue was dissolved in ethyl acetate, washed with 5% NaHCO3 and with water. Drying over MgSO4, followed by filtration and evaporation gave a crude oil, which solidified upon treatment with an ice-cold mixture (1:2) of ether and petroleum ether; yield: 83.6 g, melting point 64°-68° C.

(B)

(S)-[[3-[(Benzyloxycarbonyl)amino-2-oxo-1-azetidinyl]oxy]acetic acid, 1,1-dimethylethyl ester Method I Triphenylphosphine (26.2 g, 0.1 mol) was added to a solution of O-(t-butoxycarbonylmethyl)-α-N-(benzyloxycarbonyl)-L-serine hydroxamate (36.8 g, 0.1 mol) in 500 ml dry acetonitrile. A solution of triethylamine (20.9 ml, 0.15 mol) and carbon tetrachloride (9.7 ml, 0.1 mol) in 50 ml dry acetonitrile was added dropwise at room temperature, and the mixture was stirred overnight and evaporated in vacuo. The residue was dissolved in chloroform, washed with aqueous buffer solution pH 4 (citrate/HCl), dried over MgSO4, and filtered. The solvent was then removed under reduced pressure and the residue chromatographed on silica gel with ether/ethyl acetate (2:1). Recrystallization of the product from ether/petroleum ether gave colorless crystals; yield 20.6 g, melting point 87°-88° C.

Method II

Dry pyridine (4.75 g, 60 mmol) was added to a solution of O-(t-butyloxycarbonylmethyl)-α-N-(benzyloxycarbonyl)-L-serine hydroxamate (11.05 g, 30 mmol) in 150 ml dry dichloromethane. A solution of methanesulfonyl chloride (6.8 g, 60 mmol) in 6ml dichloromethane was dropped into this mixture at 0° C. The mixture was stirred overnight at room temperature, poured into ice-cold water and repeatedly extracted with dichloromethane. The combined organic layer was washed twice with dilute HCl, with water, 5% NaHCO₃, water and dried over MgSO₄. Filtration and concentration in vacuo yielded an oil which solidified by stirring with ether: 9.4 g; melting point 92°–94° C.

This product combined with product from a second run (total 11.2 g. 26 mmol) in 50 ml dry acetone was dropped into a refluxed suspension of anhydrous potassium carbonate (21.1 g, 0.15 mol) in 100 ml of dry acetone. The mixture was stirred vigorously and refluxed for 1.5 hour, then cooled to room temperature, filtered and evaporated in vacuo. The residue was dissolved in ether, washed with water and dried over MgSO₄. Filtration and concentration in vacuo yielded the title compound as crude which was recrystallized from ether/petroleum ether; yield 7.41 g, melting point 82°–85° C.

(C) 3S(Z)]-[[3-[[(2-Amino 4-thiazolyl)(methoxyimino)acetyl]amino]-2-oxo-1-azetidinyl]oxy]acetic acid, 1,1-dimethylethyl ester (S)-[[3-[(Benzyloxycarbonyl)amino]-2-oxo1-azetidinyl]oxy]acetic acid. 1,1-dimethylethyl ester (1.4 g, 4.0 mmol) was dissolved in 25 ml of dry dimethylformamide and hydrogenated with 1 g of 10% palladium on charcoal as catalyst. After 20 minutes the catalyst was filtered and a mixture of (Z)-2-amino-α-(methoxyimino)-4-thiazoleacetic acid (4.4 mmol). 1-hydroxybenzotriazole hydrate (0.15 g, 1.0 mmol). dicyclohexylcarbodiimide (0.81g. 4.4 mmol) and 30 ml of dry dimethylformamide was added. The mixture was stirred overnight at room temperature. The precipitated dicyclohexyl urea was filtered off and the solvent removed in vacuo. The residue was dissolved in ethyl acetate, washed with 5% NaHCO₃ and dried over MgSO₄. Filtration and evaporation in vacuo gave the title compound which solidified by stirring with ether/petroleum ether; melting point 120° C. dec.

EXAMPLES 2–5

Following the procedure of example 1C, but substituting the compound listed in column I for (Z)-2-amino-α-(methoxyimino) 4-thiazoleacetic acid, yielded the compound listed in column II.

| Column I | Column II |
| --- | --- |
| 2. (Z)-2-amino-α-[[2-(diphenyl-methoxy)-1,1-dimethyl-2-oxo-ethoxy]imino]-4-thiazoleacetic acid | [3S(Z)]-[[3-[[(2-amino-4-thiazolyl)-[[2-(diphenyl-methoxy)-1,1-dimethyl-2-oxoethoxy]imino]-acetyl]amino]-2-oxo-1-azetidinyl]oxy]acetic acid,1,1-dimethylethyl ester; the product was an oil |
| 3. (R)-α-[[(4-ethyl-2,3-dioxo-1-piperazinyl)carbonyl]-amino]benzene-acetic acid | [3S(R)]-[[3-[[[[(4-ethyl-2,3-dioxo-1-piperazinyl)-carbonyl]amino]phenyl-acetyl]amino]-2-oxo-1-azetidinyl]oxy]acetic acid, 1,1-dimethylethyl ester; melting point 100° C., dec. |
| 4. phenylacetic acid | (S)-[[3-[(phenylacetyl)-amino]-2-oxo-1-azetidinyl]oxy]acetic acid, 1,1-dimethylethyl ester; melting point 53-56° C., dec. |
| 5. α-[[[(4-methoxy-phenyl)methoxy]-carbonyl]amino]-benzeneacetic acid | (S)-[[3-[[[[(4-methoxy-phenyl)methoxy]carbonyl]-amino]phenylacetyl]-amino]-2-oxo-1-azetidinyl]-oxy]acetic acid, 1,1-dimethylethyl ester, melting point 55-62° C. |

EXAMPLE 6

(3S-trans)-[[3-[(Benzyloxycarbonyl)amino]-4-methyl2 oxo-1-azetidinyl]oxy]acetic acid, 1,1-dimethyl ester (A) O-(t-Butyloxycarbonylmethyl)-α-N (benzyloxycarbonyl)-L-threonine hydroxamate Following the procedure of example 1A, but substituting N-α-(benzyloxycarbonyl)-L-threonine for N-α-(benzyloxycarbonyl)-L-serine, yielded the title compound as an oil which was solidified by stirring overnight with dichloromethane/petroleum ether; melting point 57°–58° C.

(B)
(3S-trans)-[[3-[(Benzyloxycarbonyl)amino]-4-methyl 2-oxo-1-azetidinyl]oxy]acetic acid, 1,1-dimethylethyl ester Following the procedure of example 1B (method I), but substituting 0-(t-butyloxycarbonylmethyl)-α-N-(benzyoxycarbonyl)-L-threonine hydroxamate for O-(t-butyloxycarbonylmethyl)-α-N-(benzyloxy-carbonyl)-L-serine hydroxamate, yielded the title compound. After chromatography, the oily product crystallized after weeks of storage in a refrigerator; melting point about 30° C.

EXAMPLE 7

(S)-[[3-[(Benzyloxycarbonyl)amino]-2 oxo-1-azetidinyl]oxy]acetic acid, diphenylmethyl ester (A)
O-(Diphenylmethoxycarbonylmethyl)-α-N-(benzyloxycarbonylmethyl)-L-serine hydroxamate Following the procedure of example 1A, but substituting diphenylmethylaminoxyacetate for t-butylaminooxyacetate, yielded the title compound as a crude oil.

(B)
S)-[[3-[(Benzyloxycarbonyl)amino]-2-oxo-1-azetidinyl]oxy]acetic acid diphenylmethyl ester Following the procedure of example 1B (method II), but substituting O-(diphenylmethoxycarbonylmethyl)-α-N-(benzyloxycarbonylmethyl)-L-serine hydroxamate for O-(t-butyloxycarbonylmethyl)-α-N-(benzyloxycarbonyl)-L-serine hydroxamate, yielded the title compound, as an oil.

EXAMPLE 8

(3S-trans-2-[[3-[(Benzyloxycarbonyl)amino]-4-methyl-2-oxo-1-azetidinyl]oxy]-2-methylpropanoic acid, diphenylmethyl ester (A)
O-[1-Methyl-1-(diphenylmethoxycarbonyl)ethyl]-α-N-(benzyloxycarbonyl)-L-threonine hydroxamate Following the procedure of example 1A, but substituting N-α-(benzyloxycarbonyl)-L-threonine and diphenylmethylaminoxyisobutyrate for N-α-(benzyloxycarbonyl)-L-serine and t-butylaminoxyacetate, yielded the title compound which was dissolved in dry acetonitrile, dried over molecular sieves (3A) and evaporated in vacuo to yield a crude oil.

(B)
(3S-trans)-2-[[3-[(Benzyloxycarbonyl)amino]-4-methyl-2-oxo-1-azetidinyl]oxy]-2-methylpropanoic acid, diphenylmethyl ester Following the procedure of example 1B (method I), but substituting O-[1-methyl-1-(diphenylmethoxycarbonyl)ethyl]-α-N-(benzyloxycarbonyl)-L-threonine hydroxamate for O-(t-butyloxycarbonylmethyl]-α-N-(benzyloxycarbonyl)-L-serine hydroxamate, yielded the title compound. Recrystallization of the chromatographically purified product from ether/petroleum ether gave colorless crystals, melting point 115° C. dec.

EXAMPLE 9
(3S-trans-[[3-[(t-Butyloxycarbonyl)amino]-4-methyl-2-oxo-1-azetidinyl]oxy]acetic acid, diphenylmethyl ester (A)
O-[1-Methyl-1-(diphenylmethoxycarbonyl)ethyl]-α-N-(t-butyloxycarbonyl)-L-threonine hydroxamate Following the procedure of example 1A, but substituting N-α-(t-butyloxycarbonyl)-L-threonine and diphenylmethylaminoxyacetate for N-α-(benzyloxycarbonyl)-L-serine and t-butylaminoxyacetate. yielded the title compound, melting point 87°–92° C.

(B)
(3S-trans)-[[3-(t-Butyloxycarbonyl)amino]-4-methyl-2-oxo-1-azetidinyl]oxy]acetic acid, diphenylmethyl ester Following the procedure of example 1B (method I), but substituting O-[1-methyl-1-(diphenylmethoxycarbonyl)ethyl]α-N-(t-butyloxycarbonyl)-L-threonine hydroxamate for O-(t-butyloxycarbonylmethyl]-α-N-(benzyloxycarbonyl)-L-serine hydroxamate yielded the title compound as a colorless oil. which crystallized by stirring with Petroleum ether; melting point 73°–74° C.

EXAMPLE 10
(3S-trans)-[[3-[(Benzyloxycarbonyl)amino]-4-methyl-2-oxo-1-azetidinyl oxy]acetic acid, methyl ester (A)
O-(Methoxycarbonylmethyl)-α-N-(benzyloxycarbonyl)-L-threonine hydroxamate Following the procedure of example 1A, but substituting N-α-(benzyloxycarbonyl)-L-threonine and methylaminoxyacetate for N-α-(benzyloxycarbonyl)-L-serine and t-butylaminoxyacetate, yielded the title compound, melting point 99°–100° C.

(B)
(3S-trans)-[[3-[(Benzyloxycarbonyl)amino]-4-methyl-2-oxo-1-azetidinyl]oxy]acetic acid, methyl ester Following the procedure of example 1B (method I), but substituting O-(methoxycarbonylmethyl)-α-N-(benzyloxycarbonyl)-L-threonine hydroxamate for O-butyloxycarbonylmethyl)-α-N-(benzyloxycarbonyl)-L-serine hydroxamate yielded the title compound as a colorless oil.

EXAMPLE 11
(S)-[[3 [(Phenylacetyl)amino]-2-oxo-1-azetidinyl]oxy]acetic acid, diphenylmethyl ester (A)
0-(Diphenylmethoxycarbonylmethyl)-α-N-(phenylacetyl)-L-serine hydroxamate Following the procedure of example 1A, but substituting N-α-(phenylacetyl)-L-serine and diphenylmethylaminoxyacetate for N-α-(benzyloxycarbonyl)-L-serine and t-butylaminoxyacetate, yielded the title compound (chloroform/acetone was used as the eluent for chromatography), melting point 89°–91° C.

(B)
(S)-[[3-[(Phenylacetyl)amino]-2-oxo-1-azetidinyl]oxy]acetic acid, diphenylmethyl ester Following the procedure of example 1B (method I), but substituting O-(diphenylmethoxycarbonylmethyl)-α-N-(phenylacetyl)-L-serine hydroxamate for O-(t-butyloxycarbonylmethyl)-α-N-(benzyloxycarbonyl)-L-serine hydroxamate, yielded the title compound as a colorless oil.

EXAMPLE 12
(S)-2-[[3-[(phenylacetyl)amino]-2 oxo-1-azetidinyl]oxy]-2-methylpropanoic acid, diphenylmethyl ester (A)
O-[1-Methyl-1-(diphenylmethoxycarbonyl)ethyl]-α-N-(phenylacetyl)-L-serine hydroxamate Following the procedure of example 1A, but substituting N-α-(phenylacetyl)-L-serine and diphenylmethylaminoxyisobutyrate for N-α(benzyloxycarbonyl)-L-serine and t-butylaminooxyacetate, yielded the title compound (chloroform/acetone was used as the eluent for chromatography) as an oil, which was dissolved in dry acetonitrile dried over molecular sieves 3Å, and evaporated in vacuo.

(B)
(S)-2-[[3-[(Phenylacetyl)amino]-2-oxo-1-azetidinyl]oxy]-2-methylpropanoic acid, diphenylmethyl ester Following the procedure of example 1B (method I), but substituting O-[1-methyl-1-(diphenylmethoxycarbonyl)ethyl]-α-N-(Phenylacetyl)-L-serine hydroxamate for O-(t-butyloxycarbonylmethyl)-α-N-(benzyloxycarbonyl)-L-serine hydroxamate, yielded the title compound, melting point 63°–73° C. dec.

EXAMPLE 13
(3S-trans)-[[3-[(Phenylacetyl)amino]-4-methyl 2-oxo-1-azetidinyi]oxylacetic acid, diphenylmethyl ester (A)
O-(Diphenylmethoxycarbonylmethyl)-α-N-(phenylacetyl)-L-threonine hydroxamate Following the procedure of example 1A but substituting N-α-(phenylacetyl) L-threonine and diphenylmethyl laminoxyacetate for N-α-(benzyloxycarbonyl)-L-serine and t-butylaminoxyacetate, yielded the title compound, melting point 119°–122° C.

(B)
(3S-trans)-[[3-[(Phenylacetyl)amino]4-methyl-2-oxo-1-azetidinyl]oxy]acetic acid, diphenylmethyl ester Following the procedure of example 1B (method I), but substituting O-(diphenylmethoxycarbonylmethyl)-α-N-(Phenylacetyl)-L-threonine hydroxamate for O-(t-butyloxycarbonylmethyl)-α-N-(benzyloxycarbonyl)-L-serine hydroxamate, yielded the title compound as an oil.

EXAMPLE 14

(3S-trans)-2-[[3-[(Phenylacetyl)amino]-4-methyl-2-oxo-1-azetidinyl]oxy1-2-methylpropanoic acid, diphenylmethyl ester (A) 0-[1-Methy 1-1-(diphenylmethoxycarbonyl)ethyl]-α-N-(phenylacetyl)-L- threonine hydroxamate Following the procedure of example 1A, but substituting N-α-(phenylacetyl)-L-threonine and diphenylmethylaminoxyisobutyrat for N-α-(benzyloxycarbonyl)-L-serine and t-butylaminoxyacetate yielded the title compound, melting point 88° C.

(B) (3S-trans)-2-[[3-[(Phenylacetyl)amino-4-methyl-2 oxo-1-azetidinyl]oxy]-2 methylpropanoic acid, diphenylmethyl ester Following the procedure of example 1B (method I), but substituting O-[1 methyl-1-diphenylmethoxycarbonyl)ethyl]-α-N-(phenylacetyl)-L-threonine hydroxamate for O-(t-butyloxycarbonylmethyl)-α-N-(benzyloxycarbonyl)-L-serine hydroxamate, yielded the title compound, melting point 78° C. dec.

EXAMPLE 15

[3S(Z)]-[[3-[[(2-Amino-4-thiazolyl)(methoxyimino)acetyl]amino]-2-oxo-1-azetidinyl]oxy]acetic acid. potassium salt N-Methyl-N-trimethylsilyltrifluoroacetamide (0.20 g, 1.0 mmol) (hereinafter MSTFA) was added to a suspension of [3S(Z)]-[[3-[[(2-amino-4-thiazolyl) (methoxyimino)acetyl]amino]-2-oxo-1-azetidinyl]oxy]-acetic acid, 1,1-dimethylethyl ester (0.20 g, 0.5 mmol; see example 1) in 5 ml of dry acetonitrile at 0° C. Stirring was continued for 30 minutes at 0° C. and iodotrimethylsilane (0.10 g; 0.5 mmol) was added. After stirring for 30 minutes at room temperature the mixture was evaporated in vacuo. The residue was taken up in 5 ml of absolute ether, and 0.5 ml of methanol was added. The precipitate was filtered off 30 minutes later, suspended in 5 ml of ice-cold water and the pH was adjusted to 6.5 with 1N Potassium hydroxide. Reversed Phase chromatography of this suspension on HP-20 resin using water as eluent and freeze-drying of the appropriate fractions. yielded 120 mg of the title compound; melting Point >170° C., dec.

EXAMPLE 16

[3α(R)]-[[3-[[[[(4-Ethyl-2.3-dioxo-1-piperazinyl)-carbonyl]amino]phenylacetyl]amino]-2-oxo-1-azetidinyl]oxy]acetic acid, sodium salt Removal of the ester group from 3S(R)]-[[3-[[[[(4-ethyl-2,3-dioxo-1-piperazinyl)carbonyl]-amino]-phenylacetyl]amino]-2-oxo-1-azetidinyl]oxy]-acetic acid, 1,1-dimethylethyl ester (see example 3) was accomplished using MSTFA and iodotrimethylsilane as described in example 15. After decomposition of the crude silylated product in ether by means of methanol, 0.5 ml of propylene oxide and ice-cold water were added, and the pH was adjusted to 6.5 with 5% NaHCO₃. The organic layer was separated and the aqueous phase freeze-dried; yield after chromatography on HP-20 With 8:4 water/acetone as eluent was 230 mg; melting point >160° C., dec.

EXAMPLE 17

[3S-[3α(R),4β]]-[[3-[[[[(4-methyl-2,3-dioxo 1-piperazinyl)carbonyl]amino]phenylacetyl]amino]-4-methyl-2-oxo-1-azetidinyl]oxy]acetic acid, 1,1dimethylethyl ester (3S-trans)-[[3-[(Benzyloxycarbonyl)amino1-4-methyl-2-oxo-1-azetidinyl]oxy]acetic acid, 1 1-dimethylethyl ester (1.53 q; 4.2 mmol) (see example 6) was dissolved in 20 ml of dry dimethylformamide. After adding 1.4 g of palladium on charcoal (10%) catalyst, a stream of hydrogen was bubbled through the solution for about 1 hour. After filtration a reaction mixture (30 minutes, 0° C.) comprising (R)-α-[[(4-ethyl-2,3-dioxo-1-piperazinyl)carbonyl]amino]benzeneacetic acid (1.34g; 4.2 mmol). 1-hydroxy-benzotriazole hydrate (0.70 g) and dicyclohexylcarbodiimide (0.92 g; 4.4 mmol) in 30 ml of dry dimethylformamide was added and the mixture was stirred overnight, at room temperature. The precipitated urea was filtered off, the solvent removed in vacuo and the residue chromatographed on silica gel with ethyl acetate as eluent. The oily product crystalized by treatment with petroleum ether.

Yield: 0.25 g, melting point, 103°–110° C., dec.

EXAMPLE 18

[3S-[3α(Z).4β]]-[[3-[[(2-Amino 4-thiazolyl)-(methoxyimino)acetyl]amino]-4-methyl-2-oxo-1-azetidinyl]oxy]acetic acid, sodium salt MSTFA (0.43 ml, 2.2 mmol) was added to a solution of (3S-trans)-[[3-[(benzyloxycarbonyl)-amino]-4-methyl-2-oxo-1-azetidinyl]oxy]acetic acid, 1.1-dimethylethyl ester (0.73 g. 2.0 mmol) (see example 6) in 20 ml of dry acetonitrile at 0° C. Iodotrimethylsilane (0.56 ml, 4.4 mmol) was added 30 minutes later at 0° C. and stirring was continued for 30 minutes at room temperature. After evaporation in vacuo the residue was dissolved in 15 ml of dry tetrahydrofuran, (Z)-2-amino-α-(methoxyimino)-4-thiazoleacetic acid, 1-hydroxybenzotriazole ester (0.64 g: 2.0 mmol) was added and the mixture was stirred overnight at room temperature. The solvent was removed in vacuo. After adding ether and ice-cold water the pH was adjusted to 6.5 with NaHCO₃. The organic layer was separated and the aqueous phase freeze-dried. chromatography on HP-20 with 8:2 water-/acetone as eluent yielded the title compound (260 mg).

EXAMPLE 19

[3S-[3α(Z),4β]]-[[3-[[(2-Amino-4-thiazolyl)-[(1-carboxy-1 methylethoxy)imino]acetyl]amino]-4-methyl-2-oxo-1-azetidinyl]oxy]acetic acid. disodium salt Following the procedure of example 18, but substituting (Z)-2 amino-α-[[2-(diphenylmethoxy)- 1,1-dimethyl-2-oxoethoxy]imino]-4-thiazoleacetic acid. 1-hydroxybenzotriazole ester for (Z)-2-amino-α-(methoxyimino) -thiazoleacetic acid, 1-hydroxybenzotriazole ester, yielded [3S-[3α(Z) 4B]]-[3-[[(2-amino-4-thiazolyl)]]2-(diphenylmethoxy)-1.1-dimethyl-2-oxoethoxy ]imino]acetyl]amino]-4-methyl-2-oxo-1-azetidinyl]oxy]acetic acid, sodium salt. The product was freeze-dried and suspended in a solution of trifluoroacetic acid (10 ml) and anisole (1 ml) at −10° C. The trifuoroacetic acid was distilled off 10 minutes later at 0° C. ether and ice-cold water were added and the pH was adjusted to 6.5 by means of NaHCO₃. After freeze-drying the aqueous phase, the crude product was chromatographed on HP-20 with water as eluent; melting point 200° C., dec.

EXAMPLES 20–22

Following the procedure of example 1C, but substituting (3S-trans)-[[3-[(benzyloxycarbonyl)-amino]-4-methyl-2-oxo 1-azetidinyl oxy]acetic acid. methyl ester (see example 10) for (S)-[[3-[(benzyloxycarbonyl)amino]-2-oxo-1-azetidinyl]oxy]acetic acid, 1,1-dimethylethyl ester and the acid listed in column I for (Z)-2-amino-α-(methoxyimino)-4-thiazoleacetic acid, yielded the compound listed in column II.

| 20. | (Z)-2-amino-α-(methoxyimino)-4-thiazoleacetic acid | [3S-[3α(Z),4B]]-[[3-[[(2-amino-4-thiazolyl)-(methoxyimino)]acetyl]-amino]-4-methyl-2-oxo-1-azetidinyl]oxy]acetic acid, methyl ester: melting point 99° C., dec. |
|---|---|---|
| 21. | (Z)-2-amino-α-[[2-(diphenyl-methoxy)-1,1-dimethyl-2-oxoethoxy]imino]-4-thiazoleacetic acid | [3S-[3α(Z),4B]]-[[3-[[(2-amino-4-thiazolyl)-[[2-(diphenylmethoxy)-1,1-dimethyl-2-oxoethoxy]-imino]acetyl]amino]-4-methyl-2-oxo-1-azetidinyl]-oxy]acetic acid, methyl ester; melting point 88–90° C., dec. |
| 22. | (R)-α-[[(4-ethyl-2,3-dioxo-1-piperazinyl)carbonyl]-amino]benzeneacetic acid | [3S-[3α(R),4β]]-[[3-[[[[(4-ethyl-2,3-dioxo-1-piperazinyl)carbonyl]-amino]phenylacetyl]amino]-4-methyl-2-oxo-1-azetidinyl]oxy]acetic acid, methyl ester; melting point 100° C., dec. |

EXAMPLE 23

[3S-[3α(Z), 4β]]-[[3-[[(2-amino-4-thiazolyl)-[(1-carboxy-1-methylethoxy)imino]acetyl]amino]-4-methyl-2-oxo-1-azetidinyl]oxy]acetic acid, methyl ester, sodium salt Using trifluoroacetic acid, anisole and sodium bicarbonate (as described in example 19), the title compound was prepared from 3S-[3α(Z),-4β1]-[[3-[[(2-amino-thiazolyl)[[2-(diphenylmethoxy)-1,1 dimethyl-2-oxoethoxy]imino]acetyl]-amino]-4-methyl-2-oxo-1-azetidinyl]oxy]acetic acid, methyl ester; melting point about 192° C., dec.

EXAMPLE 24

[3S-3α(R),4β]]-[[3-[[[[[(4-Methoxyphenyl)methoxy]-carbonyl]amino]phenylacetyl]amino]-4-methyl-2-oxo-1-azetidinyl]oxy]acetic acid (3S-trans)-[[3-[(t-Butyloxycarbonyl)amino]-4-methyl-2-oxo-1-azetidinyl]oxy]acetic acid. diphenylmethyl ester (4.4 g1 10.0 mmol) was dissolved in a solution of 33 ml of trifluoroacetic acid and anisole (3.3 ml; 30.0 mmol) at −10° C. The mixture was evaporated in vacuo 10 minutes later and the residue was stirred with ether, filtered off and dried over P₂O₅ to give colorless crystals of (3S)-[[3-amino-4-methyl-2-oxo-1-azetidinyl]oxy]acetic acid, trifluoroacetate salt (yield 2.87 g). The salt (2.87 g; 10.0 mmol) was suspended in dry acetonitrile. MSTFA (5.57 ml; 30.0 mmol) was added and stirring was continued for 30 minutes. After evaporating in vacuo the residue was dissolved in dry tetrahydrofuran and then added to a mixture of the [[[(4-methoxyphenyl)methoxy]-carbonyl]amino]benzeneacetic acid 1-hydroxybenzotriazole ester (4. g, 10.0 mmol) in 25 ml of dry tetrahydrofuran at 0° C., stirred overnight at room temperature and evaporated in vacuo. After adding ether the crude silylated product was decomposed with 1 ml methanol. After removing the solvents in vacuo the residue was stirred with ether/petroleum ether to give colorless crystals of the title compound.

EXAMPLE 25

(S)-[[2-Oxo-3-[(Phenylacetyl)amino]-1-azetidlnyl-oxy]acetic acid, sodium salt (S)-[[3-[(Phenylacetyl)amino]-2-oxo-1-azetidinyl]oxy]acetic acid, diphenylmethyl ester 1.78 g, 4.0 mmol) (see example 11 was dissolved in 30 ml of absolute methanol and hydrogenated with 1.2 g of 10% palladium on charcoal as catalyst. After 10 minutes the catalyst was filtered off and the filtrate was evaporated in vacuo. The residue was dissolved in a mixture of ether and ice-cold water and the pH was adjusted to 6 5 With NaHCO₃. Reverse phase chromatography of the freeze-dried aqueous phase on HP-20 with water/acetone as eluent and freeze-drying of the appropriate fractions yielded 255 mg of the title compound, melting point 56°–70° C. dec.

EXAMPLE 26

(S)-2-[[2-Oxo-3-[(phenylacetyl)amino]-1-azetidinyl]oxy]-Z-methylpropanoic acid, sodium salt Following the procedure of example 25, but substituting 4.0 mmol of (S)-2-[[3-[(phenylacetyl)amino]-2-oxo-1-azetidinyl]oxy]-2 methylpropanoic acid, diphenylmethyl ester (see example 12) for 4.0 mmol of (S)-[[3 [(phenylacetyl amino]-2-oxo-1-azetidinyl]oxy]acetic acid, diphenylmethyl ester yielded 630 mg of the title compound, melting point 88° C.

EAMPLE 27

(3S-trans)-[[4-Methyl-2-oxo-3-[(phenylacetyl)amino]-1-azetidinyl]oxy]acetic acid, sodium salt Following the procedure of example 25, but substituting (3S-trans)-[[3-[(phenylacetyl)amino]-4-methyl-2-oxo-1-azetidinyl]oxy]acetic acid, diphenylmethyl ester (see example 13) for (S)-[[3-[(phenylacetyl)amino]-2-oxo-1-azetidinyl]oxy]acetic acid, diphenylmethyl ester yielded the title compound, melting point 77°–130° C., dec.

EXAMPLE 28

(3S-trans)-2-[[4-Methyl-2-oxo-3-[(phenylacetyl)-amino]-1 azetidinyl]oxy]-2-methylpropanoic acid. sodium salt Following the procedure of example 15, but substituting (3S-trans)-2-[[3-[(phenylacetyl)-amino]-4-methyl-2-oxo-1-azetidinyl]oxy]-2-methylpropanoic acid, diphenylmethyl ester (see example 14) for (S)- [[(phenylacetyl)amino]-2-oxo-1-azetidinyl]oxy acetic acid, diphenylmethyl ester, yielded the title compound, melting point 135°–115° C., dec.

EXAMPLE 29

(3S-trans)-2-[[3-(Benzyloxycarbonyl)amino]-4-methyl-2-oxo-1-azetidinyl]oxy]-2-methylpropanoic acid (3S-trans)-2-[[3-[(Benzyloxycarbonyl)amino-4-methyl 2-oxo-1-azetidinyl]oxy]-2-methylpropanoic acid, diphenylmethyl ester (1.51 g; 3.0 mmol) (see example 8) was stirred with a solution of 1 ml of anisole in 10 ml of trifluoroacetic acid at −10° C. for 10 minutes. The mixture was evaporated n vacuo, and the residue was dissolved in ether. After adding petroleum ether the resulting precipitate was collected: yield 0.85 g, melting point 125°–126° C., dec.

EXAMPLE 30

[3S-3α(Z),4β))-2-[[3-([(2-Amino-1-thiazolyl)-(methoxyimino) acetyl]amino]-4-methyl-2-oxo-1-azetidinyl]oxy]-2-methylpropanoic acid, sodium salt Following the procedure of example 18 but substituting (3S-trans)-2-[[3-[benzyloxycarbonyl)-amino]-4-methyl-2-oxo-1-azetidinyl]oxy]-2-methyl-propanoic acid (see example 29 for 3S-trans)-[3-[(benzyloxycarbonyl)amino-4-methyl-2-oxo-1-azetidinyl]oxy]acetic acid, 1,1-dimethylethyl ester, yielded the title compound, melting point >190° C., dec.

EXAMPLE 31

(3S-trans)-2-[[3-[(Benzyloxycarbonyl)amino]-4-methyl-2-oxo-1-azetidinyl]oxy]-2-methylpropanoic acid, methyl ester To a stirred suspension of (3S-trans)-2-[[3-(benzyloxycarbonyl)amino4-methyl-2-oxo-1-azetidinyl]oxy]-2-methylpropanoic acid (1.68 g, 5.0 mmol) (see example 29) in 10 ml of dry dichloromethane were added 4 dimethylaminopyridine (30 mg), dry methanol 0.81 ml, 210 mmol) and dicyclohexylcarbodiimide (1.13 g, 5.5 mmol) at 0° C. The reaction mixture was stirred for 3 hours at room temperature. The precipitate (dicyclohexylurea) was removed by filtration and the filtrate was evaporated in vacuo. The residue was taken up in ether, filtered, washed with aqueous buffer solution pH 4 (citrate/HCl), NaHCO3 solution, dried over MgSO4 and filtered. Evaporation in vacuo gave the title compound.

EXAMPLE 32

[3S-[3α(Z),4β]]-2-[[3-[[(2-Amino-4-thiazolyl)-[[(1-carboxy-1-methyl)ethoxy]imino]acetyl]amino]-4-methyl-2-oxo-1-azetidinyl]oxy -2-methylpropanoic acid, methyl ester, sodium salt Following the procedures of examples 1C and 23, but starting with (3S-trans)-2-[[-3-[(benzyloxycarbonyl)amino]-4-methyl-2-oxo-1-azetidinyl]oxy]-2-methylpropanoic acid, methyl ester see example 31), yielded the title compound, melting point >150° C., dec.

EXAMPLE 33

(3S-trans)-[[3-[(t-Butyloxycarbonyl)amino]-4-methyl-2-oxo-1-azetidinyl]oxy]acetic acid, diphenylmethyl ester (A)

(3S-trans)-3-(t-Butyloxycarbonylamino)-I-hydroxy-4-methyl-2-azetidinone (10.2 g, 33.3 mmol) was dissolved in dry methanol and hydrogenated with 1.66g of palladium on carbon (10%) as catalyst. After 45 minutes the catalyst was filtered off and the filtrate was evaporated to dryness at reduced pressure. Stirring of the residue (6.94 g) with ether-petroleum ether gave the title compound; yield 6.60 g, melting point >144° C., dec.

(B)

(3S-trans)-[[3-[(t-Butyloxycarbonyl)amino]-4-methyl-2-oxo-1-azetidinyl]oxy]acetic acid, diphenylmethyl ester Triethylamine (0 61 g, 6.0 mmol was dropped into a solution of (3S-trans)-3-(t-butyloxy-carbonylamino)-1-hydroxy-4-methyl-2-azetidinone (1.08 g. 5.0 mmol) and diphenylmethylchloroacetate (1.43 g. 5.5 mmol) in 10 ml of dry dimethylformamide. The mixture was stirred overnight at room temperature. The precipitate was removed by filtration and the solvent was stripped in vacuo. The residue was taken up in ethyl acetate, filtered, washed with 5% NaHCO3 solution and with water, dried over MgSO4 and evaporated in vacuo to give a colorless oil; yield 2.0 g. By storing in a refrigerator the title compound crystallized, melting point 73°–74° C.

EXAMPLE 34

(3S-trans)-[[3-[(t-Butyloxycarbonyl)amino]-4-methyl-2-oxo-1-azetidinyl]oxy]acetic acid, 1,1-dimethylethyl ester Following the procedure of example 33B, but substituting t-butylchloroacetate for diphenylmethylchloroacetate yielded the title compound as an oil, which crystallized upon storage an a refrigerator.

EXAMPLE 35

(3S-trans)-[(3-Amino-4-methyl-2-oxo-1-azetidinyl)-oxy]acetic acid, 1,1-dimethylethyl ester (3S-trans)-[[3-[(t-Butyloxycarbonyl)amino]-4-methyl-2-oxo-1-azetidinyl]oxy]acetic acid 1,1-dimethylethyl ester (1.44 g, 4.4 mmol) (see example 34) was dissolved in a mixture of 8.8 ml of trifluoroacetic acid and 0.88 ml of anisole at −10° C. The solution was evaporated in vacuo 10 minutes later at 0° C., and the residue was stirred with ether, filtered off and dried over P2O5 to give colorless crystals of the trifluoroacetate salt of the title compound; yield 0.61 g, melting point 111°–112° C., dec.

The salt (1.38 g. 4.0 mmol) was suspended in dry acetonitrile at 0° C. N-Methyl-N-trimethylsilyltrifluoroacetamide (1.56 m 8.0 mmol) was added and stirring was continued for 30 minutes at room temperature. After addition of methanol (0.32 ml, 8.0 mmol) at 0° C. the precipitation of the title compound was completed by adding dry ether. The colorless precipitate was collected and dried over P2O5; yield 0.92 g, melting point >115° C., dec.

EXAMPLE 36

[3S-[3α(R),4β]]-[[3-[Amino(phenylacetyl)amino]-4-methyl-2-oxo-1-azetidinyl]oxy]acetic acid The sodium salt of [3S-[3α(R),4β]]-[[3[[[[[(4-methoxyphenyl)methoxy]carbonyl]amino]-phenylacetyl]amino]-4-methyl-2-oxo-1-azetidinyl]-oxy]acetic acid (0.493g, 1.0 mmol) (prepared from the crude acid by means of NaHCO$_3$ followed by purification on HP-20) was dissolved in a mixture of trifluoroacetic acid (2 ml) and anisole (0.2 ml) at −10° C. The solution was evaporated in vacuo 10 minutes later at 0° C. and the residue was stirred with ether to give the trifluoroacetate salt of the title compound, melting point >55° C., dec.

To a suspension of the salt (0.21 g; 0.5 mmol) in 4 ml of dry acetonitrile. MSTFA (0.29 ml, 1,5 mmol) was added at 0° C. The resulting solution was allowed to warm to room temperature and cooled to 0° C. again 30 minutes later. Dry methanol (0.06ml, 1.5mmol) was added and the title compound was precipitated by addition of dry ether collected by filtration and dried in vacuo over P$_2$O$_5$; yield 0.11 g.

EXAMPLE 37

(3S-trans)-[[3-[[(Phenylacetyl)amino]-4-methyl-2-oxo-1-azetidinyl]oxy]acetic acid, 2,2-dimethyloropionyloxy methyl ester (3S-trans)-[[4-Methyl-2-oxo-3-[(phenylacetyl)-amino]-1 azetidinyl]oxy]acetic acid, sodium salt (0.94 g; 3.0 mmol) (see example 27), was dissolved in 20 ml of dimethylformamide. Iodomethylpivalate (1.45 g; 6.0 mmol) was added at +10° C. and the mixture was stirred overnight at room temperature. The solvent was stripped in vacuo and the residue was taken up in ethyl acetate, washed successively with water, NaHCO$_3$ solution, water and then dried (Na$_2$SO$_4$). After removal of the solvent in vacuo, the resulting oil was stirred with petroleum ether and the insoluble oil was separated (0.86 g) and then purified by chromatography on SiO$_2$ with a mixture of ethyl acetate/ether (1:3) as eluent to give a colorless oil; yield 0.43 g.

EXAMPLE 38

(3S-cis)-[(3-Amino-4-methyl-2-oxo-1-azetidinyl)-oxy]acetic acid, trifluoroacetate salt

(A)
O-(Diphenylmethoxycarbonylmethyl)-N-t-butyloxycarbonyl-allo-L-threonine

Following the procedure of example 1A, but substituting N-t-butyloxycarbonyl allo-L-threonine and diphenylmethylaminoxyacetate for N-α-(benzyloxycarbonyl)-L-serine and t-butylaminooxyacetate, yielded the title compound. melting point 140°–143° C.

(B) (3S-cis)-[[3-[( -Butoxycarbonyl)amino]-4-methyl 2-oxo-azetidinyl]oxy]acetic acid. diphenylmethyl ester Following the procedure of example 1B (method I), but substituting O-(diphenylmethoxycarbonylmethyl)-N-t-butyloxycarbonyl-allo-L-threonine for O-(t-butyloxycarbonylmethyl)α-N-(benzyloxycarbonyl) L-serine hydroxamate, yielded the title compound. After chromatography on silica gel using ethyl acetate/ether as eluent, the oily product was solidifed by stirring with petroleum ether; melting point 105°–108° C.

(C)
(3S-cis)-[(3-Amino-4-methyl-2-oxo-1-azetidinyl)oxy]acetic acid, trifluoroacetate salt (3S-cis)-[[3-[-Butoxycarbonyl)amino]-4-methyl-2-oxo-1-azetidinyl]oxy]acetic acid diphenylmethyl ester 1.5 g, 3.5 mmol) was dissolved in a mixture of 15 ml of trifluoroacetic acid and 1.5 ml of anisole at −10° C. After standing at 0° C. for 10 minutes. 30 ml ether was added. The precipitate was filtered, washed with ether and dried in vacuo over P$_2$O$_5$ to give a hygroscopic solid; yield 0.53 g.

EXAMPLE 39

(3S-trans1-[[3-[(t-Butyloxycarbonyl)amino]-4-methyl-2-oxo-1-azetidinyl]oxy]acetic acid, phenylmethyl ester

(A)
N$^2$(t-Butyloxycarbonyl)-N-(phenylmethoxy)-L-threonineamide

N-(t-Butyloxycarbonyl)-L-threonine (82.2 g) was dissolved in 1 liter of ethyl acetate and 40.5 g of dimethyl (phenylmethyl)amine was added. After stirring for 10 minutes the mixture was cooled to −10° C. and 31.05 g of methyl chloroformate were added dropwise. The mixture was stirred for 30 minutes at −10° C., after which a solution of 40.65 g of (phenylmethoxy)amine in 300 ml of ethyl acetate was added at −10° C. The temperature was then permitted to rise to 5° C. during a 90 minute period. The reaction mixture was evaporated in vacuo and redissolved in 1 liter of ethyl acetate the insoluble material was filtered off and the filtrate washed, with cooling, with water, dilute hydrochloric acid, (pH of aqueous phase not less than 2.5), sodium bicarbonate solution and brine. After drying (MgSO$_4$) the solvent was removed in vacuo to yield an oil, which crystallized on treatment with petroleum ether, yielding 79.4 g of the title compound, melting point 87° C.

(B)
N$^2$-(t-Butyloxycarbonyl)-O-(methylsulfonyl)-N-(phenylmethoxy)-L-threonineamide N$^2$-(t Butyloxycarbonyl)-N-(Phenylmethoxy)-L-threonineamide (244 g) was dissolved in 1.2 liters of pyridine and the solution was cooled to 0° C. With stirring 120 grams of methanesulfonyl chloride was added dropwise at 0°–5° C. After 2.5 hours, the reaction mixture was poured into a mixture of 1500 ml of 2N hydrochloric acid and ice and concentrated HCl was added to adjust the pH of the mixture to 4. The title compound crystallized, and, after stirring for 1 hour, was filtered off, washed with water and petroleum ether. After drying at room temperature the yield was 356.4 grams, which contained a considerable amount of water, melting point 128°–130° C. dec.

(C)
(3S-trans)-3-[(t-Butyloxycarbonyl)amino]-4-methyl-2-oxo-1-(phenylmethoxy)azetidine Potassium carbonate (200g) was dissolved in 300ml of water, 1.5 liters of 1,2-dichloroethane was added, and the mixture was refluxed. A suspension of 178 g of N$^2$-(t-Butyloxycarbonyl)-O-(methylsulfonyl)-N-(phenylmethoxy)-L-threonineamide in 1.2-dichloroethane was added and the mixture was refluxed for 2 hours. The layers were cooled and the organic layer was evaporated, redissolved in ethyl acetate, washed twice with water, dried (MgSO$_4$) and evaporated again.

The oily residue crystallized on treatment with petroleum ether, yielding 76.7 g of the title compound, melting point 78° C.

(D)

(3S-trans)-1-Hydroxy-3-[(t-butyloxycarbonyl)-amino4-methyl-2-azetidinone (3S trans)-3-((t-Butyloxycarbonyl)amino]-4-methyl-2-oxo-1-(phenylmethoxy)azetidine was catalytically hydrogenated to the title compound using the procedure of Mattingly et al. J. Org. Chem.. 45:410 (1980).

(E)

(3S-trans)-[[3-[(t-Butyloxycarbonyl)amino]-4-methyl-2-oxo-1-azetidinyl]oxy]acetic acid. phenylmethyl ester (3S-trans)-1-Hydroxy-3-[(t-butyloxycarbonyl)-amino]-4-methyl-2-azetidinone (21.6g) was dissolved in 300ml of dimethylformamide, 25.2g of bromoacetic acid. phenylmethyl ester was added. 17 ml of triethylamine was added. and the mixture was stirred for 3 hours at room temperature. The resulting precipitate was filtered off. The filtrate evaporated in vacuo, the residue dissolved in ethyl acetate and the solution treated with water, the pH of which was adjusted to 7. The organic phase was washed twice with water, dried (MgSO$_4$) and evaporated to yield 33.4g of the title compound as an oil.

EXAMPLES 40–50

Following the procedure of example 39, but substituting the appropriate ester for bromoacetic acid, phenylmethyl ester, yielded the compounds listed below.

40. (3S-trans)-[[3-[(t-butyloxycarbonyl)amino]-4-methyl-2-oxo-1-azetidinyl]oxy]acetic acid ethyl ester 41. (3S-trans)-[[3-[(t-butyloxycarbonyl)amino]-4-methyl-2-oxo-1-azetidinyl]oxy]acetic acid. 2-hydroxyethyl ester 42. (3S-trans)-[[3-[(t-butyloxycarbonyl)amino]-4-methyl-2-oxo-1-azetidinyl]oxy]acetic acid, 2-methoxyethyl ester 43. (3S-trans)-[[3-[(t-butyloxycarbonyl)amino]-4-methyl-2-oxo-1-azetidinyl]oxy]acetic acid 2-methylpropyl ester 44. (3S-trans)-[[3-[(t-butyloxycarbonyl)amino]-4-methyl-2-oxo-1-azetidinyl oxy]acetic acid. 1-ethylpropyl ester 45. (3S-trans)-[[3-[(t-butyloxycarbonyl)amino]-4-methyl-2-oxo-1-azetidinyl]oxy]acetic acid, phenyl ester 46. (3S-trans)-[[3-[(t-butyloxycarbonyl)amino]-4-methyl-2-oxo-1-azetidinyl]oxy]acetic acid, 2-methylphenyl ester 47. (3S-trans)-[[3-[(t-butyloxycarbonyl)amino]-4-methyl-2-oxo-1-azetidinyl]oxy]acetic acid, 5-indanyl ester 48. (3S-trans)-[[3-[(t-butyloxycarbonyl)amino]-4-methyl-2-oxo-1-azetidinyl]oxy]acetic acid, 2-indanyl ester 49. (3S-trans)-[[3-[(t-butyloxycarbonyl)amno]-4-methyl-2-oxo-1-azetidinyl]oxy]acetic acid, (5-methyl-2 oxo-1,3-dioxol-4-yl)methyl ester 50. (3S-trans)-[[3-[(t-butyloxycarbonyl)amino]-4-methyl-2-oxo-1-azetidinyl]oxy]acetic acid, (2,2-dimethyl-1-oxopropoxy)methyl ester

EXAMPLE 51

(3S-trans)-[(3-Amino-4-methyl-2-oxo-1-azetidinyl)-oxy]acetic acid, phenylmethyl ester, trifluoroacetate salt (3S-trans) -[[3-[(t-Butyloxycarbonyl)amino]-4-methyl-2-oxo-1-azetidinyl]oxy]acetic acid. phenylmethyl ester (3.6g) was dissolved in 5 ml of dichloromethane and the solution was cooled to −10° C. Trifluoroacetic acid (25ml) was added dropwise and the mixture was stirred for 20 minutes at −10° C. After evaporation, the residue was treated with ether yielding 2.5 g of the title compound.

EXAMPLES 52–62

Following the procedure of example 51, but substituting the appropriate ester for (3S-trans)-[[3-[(t-Butyloxycarbonyl)amino]-4-methyl-2-oxo-1-azetidinyl]oxy]acetic acid phenylmethyl ester, yielded the compounds listed below.

52. (3S-trans)-[(3-amino-4-methyl-2-oxo-1-azetidinyl)oxy]acetic acid, ethyl ester, trifluoroacetate salt 53. (3S-trans)-[(3-amino-4-methyl-2-oxo-1-azetidinyl)oxy]acetic acid, 2-hydroxyethyl ester, trifluoroacetate salt 54. (3S-trans)-[(3-amino-4-methyl-2-oxo-1-azetidinyl)oxy]acetic acid, 2-methoxyethyl ester, trifluoroaoetate salt 55. (3S-trans)-[(3-amino-4-methyl-2-oxo-1-azetidinyl)oxy]acetic acid, 2-methylpropyl ester, trifluoroacetate salt 56. (3S-trans)-[(3-amino-4-methyl-2-oxo-1-azetidinyl)oxy]acetic acid, 1-ethylpropyl ester, trifluoroacetate salt 57. (3S-trans)-[(3-amino -methyl-2-oxo-1-azetidinyl)oxy]acetic acid, phenyl ester, trifluoroacetate salt 58. (3S-trans)-[(3-amino-4-methyl-2-oxo-1-azetidinyl)oxy]acetic acid, 2-methylphenyl ester, trifluoroacetate salt 59. (3S-trans)-[(3-amino-4-methyl-2-oxo-1-azetidinyl)oxy]acetic acid. 5-indanyl ester, trifluoroacetate salt 60. (3S-trans)-[(3-amino-4 methyl-2 oxo-1-azetidinyl)oxy]acetic acid 2-indanyl ester, trifluoroacetate salt 61. (3S-trans)-[(3-amino-4-methyl-2-oxo-1azetidinyl)oxy]acetic acid, (5-methyl-2-oxo-1,3-dioxol-4-yl)methyl ester, trifluoroacetate salt 62. (3S-trans)-[(3-amino-4-methyl-2-oxo-1-azetidinyl)oxy) acetic acid, (2,2-dimethyl-1-oxo-ethoxy)methyl ester, trifluoroacetate salt

EXAMPLE 63

[3S-[3α(Z),4β])-[[3-[[(2-Amino-4-thiazolyl)-(methoxyimino)acetyl]amino]-4-methyl-2-oxo-1-azetidinyl]oxy]acetic acid, phenylmethyl ester (Z)-2-Amino-α-(methoxyimino)-4-thiazoleacetic acid (1.32g) was dissolved in 22ml of absolute dimethylformamide, 1 1 mole of triethylamine was added, and the mixture was cooled to −25° C. Diphenyl phosphochloridate (1.36 ml) was added and the temperature kept at −25° C. for 50 minutes. This mixture was added to a solution prepared from 2.5 g of (3S-trans)-[(3-amino-4-methyl-2-oxo-1-azetidinyl)oxy]acetic acid. phenylmethyl,ester, trifluoroacetate salt and 4.6 ml of triethylamine in 22 ml of dimethylformamide, also cooled to −25° C. The reaction mixture was stirred at −25° C. for 2.5 hours, added with stirring to 70ml of 0.5 molar monobasic potassium phosphate, diluted with 70ml of water and layered with ethyl acetate. The pH was adjusted to 6 by adding 2N hydrochloric acid. The aqueous phase was again extracted with ethyl acetate, the combined organic phases washed with water, dried with MgSO4, filtered and evaporated to yield 2,3 of the title compound as a foam, which was treated with petroleum ether and filtered.

EXAMPLES 64–66

Following the procedure of example 63, but substituting the appropriate ester for (3S-trans)-[(3-amino-4-methyl-2-oxo-1-azetidinyl)oxy]acetic acid, phenylmethyl ester, trifluoroacetate salt, yielded the compounds listed below.

64. [3S-[3α(Z),4β]]-[[3-[[(2-amino-4-thiazolyl)-(methoxyimino)acetyl]amino]-4-methyl-2-oxo-1-azetidinyl]oxy]acetic acid, (5-methyl-2-oxo-1,3-dioxol-4-yl)methyl ester 65. [3S-[3α(Z),4β]]-[[3-[[(2-amino-1-thiazolyl)-(methoxyimino)acetyl]amino]-4-methyl-2-oxo-1-azetidinyl]oxy]acetic acid, (2,2-dimethyl-1-oxopropoxy)methyl ester 66. [3S-[3α(Z),4β]][[3-[[(2-amino-4-thiazolyl)-methoxyimino)acetyl]amino]-4-methyl-2-oxo-1-azetidinyl]oxy]acetic acid, [(1-methylethyl)carbamoyl]methyl ester

EXAMPLE 67

[3S-[3α(Z),4β]]-[[3-[[(2-Amino 4 thiazolyl)-(methoxyimino)acetyl]amino]-4 methyl-2-oxo-1-azetidinylloxy]acetic acid, phenyl ester (3S-trans)-[(3-amino 4-methyl-2-oxo-1-azetidinyl)oxy]acetic acid phenyl ester, trifluoroacetate salt (2.1 g) was suspended in 50 ml of acetonitrile and 2.1 g of N-methyl(trimethylsilyl)trifluoromethylacetamide was added to yield a solution. After cooling to 0° C. (Z)-2-amino-α-(methoxyimino)-4-thiazoleacetic acid. N-hydroxybenzotriazole ester. was added. The mixture was stirred for 3 hours at room temperature. evaporated in vacuo, redissolved in ethyl acetate, washed (cooling) with brine which was adjusted to pH 7 while washing. The organic phase was dried (MgSO4), evaporated and the residue treated with ether to yield 2.6 g of the title compound.

EXAMPLES 68–73

Following the procedure of example 67 but substituting the appropriate ester for (3S-trans)-[(3-amino 4-methyl-2-oxo-1-azetidinyl)oxy]acetic acid. phenyl ester, trifluoroacetate salt, yielded the compounds listed below.

68. [3S-[3α(Z),4β]]-[[3-[[(2-amino-4-thiazolyl)-(methoxyimino)acetyl]amino]-2-oxo-1-azetidinyl]oxy]-acetic acid, ethyl ester 69. [3S-[3α(Z),4β]]-[[3-[[(2-amino-4-thiazolyl)-(methoxyimino)acetyl]amino]-2-oxo-1-azetidinyl]oxy]-acetic acid, 2-hydroxyethyl ester 70. [3S-[3α(Z),4β]- [3-[[(2-amino-4-thiazolyl)-(methoxyimino)acetyl]amino]-2-oxo-1-azetidinyl]oxy]-acetic acid, 2-methoxyethyl ester 71. [3S-[3α(Z),4β]]-[[3-[[(2-amino-4-thiazolyl)-(methoxyimino)acetyl]amino]-2-oxo-1-azetidinyl]oxy]acetic acid, 2-methylpropyl ester 72. [3S-[3α(Z),4β8]]-[[3-[[(2-amino-4-thiazolyl)-(methoxyimino)acetyl]amino -2-oxo-1-azetidinyl]oxy]-acetic acid 1-ethylpropyl ester 73. [3S-[3α(Z).4β]]-[[3-[[(2-amino-4-thiazolyl)-(methoxyimino)acetyl]amino]-2-oxo-1-azetidinyl]oxy]-acetic acid 2-indanyl ester

EXAMPLE 74

(3S-trans)-[[3-[(t-Butyloxycarbonyl)amino]-4-methyl-2-oxo-1-azetidinyl]oxy]acetic acid, potassium salt (3S-trans)-[[3-[(t-Butyloxycarbonyl)amino]-4-methyl-2-oxo-1-azetidinyl]oxy]acetic acid, phenylmethyl ester (3.6 g) was dissolved in 100 ml of methanol. After treatment with charcoal, 1.8 g of 5 percent palladium on charcoal was added and hydrogen was passed through the stirred mixture at room temperature. After 1 hour, the mixture was filtered, and the filtrate was diluted with water. neutralized with potassium carbonate and lyophilized yielding the title compound.

EXAMPLE 75

(3S-trans)-[[3-[(t-Butyloxycarbonyl)amino]-4-methyl-2-oxo-1-azetidinyl]oxy]acetic acid. (2,2-dimethyl-1 oxopropoxy)methyl ester (3S-trans)-[[3-[(t-Butyloxycarbonyl)amino]-4-methyl-2-oxo-1-azetidinyl]oxy]acetic acid. potassium salt (0.01 mole) was dissolved in 40 ml of dimethylformamide. The solution cooled to 0° C., 0.7 ml of triethylamine was added. and 3.1 g of 2.2-dimethylpropionic acid, iodomethyl ester was then added. After stirring overnight at 0° C., the solvent was removed in vacuo, and the oily residue was dissolved in 100ml of ethyl acetate, washed three times with ice water, dried (MgSO4) and evaporated to yield 2.4 g of the title compound.

EXAMPLES 76–78

Following the procedure of example 75, but substituting the appropriate compound for 2.2-dimethylpropionic acid, iodomethyl ester, yielded the compounds listed below.

76. 3S-trans)-[[3-[(t-butyloxycarbonyl)amino]-4-methyl-2-oxo-1-azetidinyl]oxy]acetic acid, (5-methyl-2-oxo-1,3-dioxol-4-yl)methyl ester 77. (3S-trans)-[[3-[(t-butyloxycarbonyl)amino]-4-methyl-2-oxo-1-azetidinyl]oxy]acetic acid. [(1-methylethyl)carbamoyl]methyl ester 78. (3S-trans)-[[3-[(t-butyloxycarbonyl)amino]-4-methyl-2-oxo-1-azetidinyl]oxy]acetic acid. [(2.2-dimethylethyl)carbamoyl]methyl ester

EXAMPLE 79

(S)-[[3 [(Benzyloxycarbonyl)amino]-2 oxo-1-azetidinyl]oxy]acetic acid (S)-[[3-[(Benzyloxycarbonyl)amino]-2-oxo-1-azetidinyl]oxy]acetic acid. Diphenylmethyl ester (15.4 g; see example 7) was mixed with 4ml of anisole. At 0° C., 40 ml of trifluoroacetic acid was added slowly and the mixture was kept at this temperature for 10 minutes. The reaction mixture was evaporated in vacuo at room temperature, dissolved in ethyl acetate and again evaporated. The oily residue was dissolved in 100 ml of ethyl acetate. ice-cold water was added and the pH of the mixture was adjusted 6.5. The ethyl acetate phase was extracted once more with diluted sodium bicarbonate solution.

The combined aqueous phases were cooled (ice), layered with b 100 ml of ethyl acetate and acidified to pH 2 with 2N hydrochloric acid. The aqueous phase was extracted two additional times with ethyl acetate, the combined ethyl acetate extracts were dried (MgSO4) and evaporated to yield 6 g of the title compound as a syrup.

The title compound was dissolved in a mixture of methanol and water. The solution adjusted to pH 6.5 with dilute sodium hydroxide and freeze dried to yield the corresponding sodium salt as an amorphous solid.

EXAMPLE 80

(S)-[[3-[(Benzyloxycarbonyl)amino)-2-oxo-1-azetidinyl-]oxy]acetic acid, (2,2-dimethyl-1-oxopropoxy)methyl ester (S)-[[3-[(Benzyloxycarbonyl)amino]-2-oxo-1-azetidinyl]oxy]acetic acid (3 g; see example 79) was dissolved in 200 ml of dimethylformamide and the solution was cooled to 0° C. 1,8-diazabicyclo[5.4.0]-undec-7-ene (0.01 mol) was added followed by 2.7 g of 2,2-dimethylpropionic acid, iodomethyl ester. After 10 minutes, the mixture was diluted with 75ml of ethyl acetate, cooled (ice-water), washed with ice-cold water, ice-cold diluted sodium bicarbonate solution and again with ice-cold water. After drying (MgSO4) the filtrate was evaporated to yield 4g of the title compound, which crystallized on standing; melting point 73°–75° C.

EXAMPLE 81

(S)-[[3-[(Benzyloxycarbonyl)amino]-2-oxo 1-azetidinyl]oxy]acetic acid, [(2,2-dimethylethoxy)carbonyl]methyl ester Following the procedure of example 80 but substituting chloroacetic acid, 1,1-dimethylethyl ester for 2,2-dimethylpropionic acid iodomethyl ester, and allowing the reaction to proceed for 6 hours, yielded the title compound; melting point 90°–92° C.

EXAMPLE 82

[3S-(3α(Z),4β]]-[(3-([Z-(((Triphenylmethyl)amino]-4-thiazoly)][methoxyimino]acetyl]amino]-2-oxo-1-azetidinyl)oxy]acetic acid, 1-ethylpropyl ester

(A)

N-[[2-[(triphenylmethyl)amino]-4-thiazolyl]-methoxyimino]acetyl]-L-threonine

L-Threonine (11g) was suspended in 140 ml of acetonitrile. After the addition of 46 ml of bistrimethyl-silylacetamide. The mixture was refluxed for 1 hour.

(Z)-2-[(triphenylmethyl)amino]-α-(methoxyimino)-4-thiazoleacetic acid (48.4 g) was dissolved in 250ml of dimethylformamide, and 15.9 g of N-hydroxybenzotriazole and 24.1 g of dicyclohexylcarbodiimide were added. The mixture was stirred for 2 hours at room temperature. The crystals (dicyclohexylurea) were filtered off and the filtrate was evaporated in vacuo, and the residue was dissolved in 300 ml of acetonitrile and combined with the solution of silylated L-threonlne.

The mixture was stirred overnight at room temperature, filtered, evaporated in vacuo, treated with water, the pH of the aqueous phase adjusted to 7.5 and extracted with ethyl acetate. The aqueous phase was acidified to pH 2.5 by the addition of 2N hydrochloric acid. The title compound precipitated and was filtered off (46.9g).

(B)

N²-[[2-[(triphenylmethyl)amino]-4-thiazolyl-][methoxyimino]acetyl]-N-[[(diphenylmethoxy)carbonyl]-methoxy]-L-threonineamide N-[[2-[(triphenylmethyl)am[no]-4-thiazolyl]-[methoxyimino]acetyl]-L threonine was reacted with [[(diphenylmethoxy)carbonyl]methoxy]amine following the procedure described in example 39A to yield the title compound as an amorphous solid.

(C)

N²-[[2-[(triphenylmethyl)amino]-4-thiazolyl]-[[methoxyimino]acetyl]-O-(methylsulfonyl)-N-[[(diphenylmethoxy)carbonyl]-methoxy]-L-threonineamide was mesylated following the procedure described in example 39B to yield the title compound as an amorphous solid.

(D) [3S-[3α(Z), 4β]]-[[3-[[2-[[(Triphenylmethyl)-amino]-4-thiazolyl]-[methoxyimino]acetyl]amino]-2-oxo-1-azetidinyl]oxy]acetic acid, diphenylmethyl ester N²-[[2-[(Triphenylmethyl)amino]-4-thiazolyl]-[methoxyimino]acetyl]-O-(methysulfonyl)-N-[[(diphenylmethoxy)carbonyl]methoxy]-L-threonineamide was treated with potassium carbonate following the procedure described in example 39C to yield the title compound.

EXAMPLE 83

3S-[3α(Z),4β]]-[[3-[[2-[[(triphenylmethyl)amino]-4-thiazolyl[]methoxyimino]acetyl]amino]-2-oxo-1-azetidinyl]oxy]acetic acid, 1-ethylpropyl ester Following the procedure of example 82, but substituting [1-ethylpropoxy)carbonyl]methoxy]amine for [[(diphenylmethoxy)carbonyl]methoxy)amine, yielded the title compound.

EXAMPLE 84

(Alternative Preparation for Compound of Example 72) 3S-[3α(Z),4β]]-[[3-[[(2 Amino-4-thiazolyl)-(methoxyimino)acetyl]amino]-2-oxo-1-azetidinyl]oxy]acetic acid, 1-ethylpropyl ester

[3S-[3α(Z),4β]]-[[3-[[2-[[(Triphenylmethyl)-amino]4-thiazolyl][methoxyimino]acetyl]amino]-2-oxo-1-azetidinyl oxyacetic acid, 1-ethylpropyl ester (1.2 g) was dissolved in 12ml of 97% formic acid at room temperature. After stirring for 4 hours, the mixture was filtered and the filtrate mixed with 35ml of dichloromethane. Water was added, and the organic phase was washed with water and dilute sodium bicarbonate, dried (MgSO4) and evaporated to yield 0.43 g of the title compound.

EXAMPLE 85

[3S-[3α(Z),4β]]-[[3-[[(2-Amino-4-thiazolyl)-(methoxyimino)-acetyl]amino]-2-oxo-1-azetidinyl]-oxy]acetic acid, diphenylmethyl ester Following the procedure of example 84, but substituting [3S-[3α(Z),4β]]-[[3-[[2-[[(triphenylmethyl)amino]-4-thiazolyl][methoxyimino-acetyl]amino)-2-oxo-1-azetidinyl]oxy]acetic acid, diphenylmethyl ester for [3S-[3α(Z),4β]]-[[3-[[2-[(triphenylmethyl)amino]4-thiazolyl][methoxyimino-acetyl]amino]-2-oxo-1-azetidinyl]oxy]acetic acid, 1-ethylpropyl ester yields the title compound.

EXAMPLE 86

[3S-[3α(Z),4β]]-[[3-[[(2-Amino-4-thiazolyl)-(methoxyimino)acetyl]amino]-4-methyl-2-oxo-1-azetidinyl]oxy]acetic acid, (5-methyl-2-oxo-1,3-dioxol-4-yl)methyl ester

[3S-[3α(Z),4β]]-[[3-[[(2-Amino-4-thiazolyl)-(methoxyimino)acetyl]amino]-4-methyl-2-oxo-1-azetidinyl]oxy]acetic acid, sodium salt (0.95 g, see example 18) was dissolved in 25 ml of dimethylformamide, cooled to 0° C., and 0.38 g of 1.8-diazabicyclo[5.4.0 undec-7-ene was added followed by 0.83 g of 5-(bromomethyl)-2-oxo-4-phenyl-1,3-dioxole. After stirring for 4 hours, the dimethylformamide was removed in vacuo, the residue dissolved with ethyl acetate, washed with ice-cold water, sodium bicarbonate solution and brine, dried (MgSO4) and evaporated. The residue was dissolved in ethyl acetate. On addition of petroleum ether, the title compound precipitated as an amorphous solid.

EXAMPLE 87

[3S-[3α(Z),4β]]-[[3-[[(2-Amino-4-thiazolyl)-(methoxyimino)acetyl]amino]-4-methyl 2 oxo-1-azetidinyl]oxy]acetic acid, (acetyloxy)methyl ester To a solution of [3S-[3α(Z),4β]-[(3-[[(2-Amino-4-thiazolyl)(methoxyimino)acetyl]amino]-4-methyl-2-oxo-1-azetidinyl]oxy]acetic acid, sodium salt (3.2 g: see example 18) in 50 ml of dry dimethylformamide was added dropwise 1.86 g of chloromethyl acetate, with stirring which was continued for 3 days. The solvent was evaporated in vacuo, and the residue was taken up in ethyl acetate, washed successively with ice-cold water, ice-cold aqueous sodium bicarbonate and ice-cold brine, and dried over CaSO4. After filtration and removal of the solvent in vacuo, the residue was chromatographed on silica, eluting with ethyl acetate, and yielding 1.08 g of the title compound, dec. >74° C.

EXAMPLE 88

[3S-[3α(Z),4β]]-[[3-[[(2-Amino-4-thiazolyl)-(methoxyimino)acetyl]amino]-4-(azidomethyl)-2-oxo-1-azetidinyl]oxy]acetic acid, potassium salt (A) 5-(Chloromethyl)-4,5-dihydro-4-oxazolecarboxamide 114 g of chloroacetaldehyde monohydrate, and 84 g of isocyanoacetamide were dissolved in 1000 ml of methanol. The mixture was cooled to 0°-3° C. and a solution of 38 g of 1,8-diazabicyclo[5.4.0]undec-7-ene in 200 ml of methanol was added with string. At this temperature. stirring was continued for 30 minutes, and, after removal of the cooling bath, for an additional hour. The solvent was removed in vacuo and the residue refluxed twice with 1000 ml each time of ethyl acetate. The combined hot extracts were treated with charcoal, filtered while still hot and evaporated to yield the title compound as a crystalline residue, melting point 110°-112° C. after recrystallization from ethyl acetate.

(B) 4-Chloro-DL-threoninamide, hydrochloride 5-(Chloromethyl)-4,5-dihydro-4-oxazolecarboxamide was dissolved in 1500 ml of 2N hydrochloric acid and warmed to 50° C. for 2 hours. The hydrochloric acid was removed in vacuo and the residue was triturated with isopropanol to yield the title compound as brownish crystals; yield 133.9 g.

(C) 4-Chloro-DL-threonine 70 grams of 4-Chloro-DL-threoninamide, Hydrochloride was dissolved in 350 ml of water. The solution was passed through a column filled with 1.8 kg of Amberlyst 15. The column was washed with water to remove the hydrochloric acid. The material was removed from the column and warmed at 60° C. for 5 hours with stirring. After cooling, the resin was put into the column again which was then eluted with a solution of 5% trichloroacetic acid in water. The fractions containing D,L-chlorothreonine were collected, evaporated to a small volume and extracted four times with 400 ml of ether each time to remove the trichloroacetic acid. The aqueous phase was freeze dried and the residue dissolved in 200 ml of isopropanol from which the title compound crystallized (yield 27 grams). A second crop of 7 grams of product was obtained from the mother liquor by evaporation, treating the oily residue with ether, removing the ether and treating the insoluble material with isopropanol again.

(D) N-(t-Butyloxycarbonyl)-4-chloro-DL-threonine 22 grams of 4-Chloro-DL-threonine Was suspended in a mixture of 43 ml of water and 71 ml of t-butanol. By the addition of 2N sodium hydroxide the pH was adjusted to 7.0, 34.3 g di-tert.-butylpyrocarbonate was added and the pH of the mixture was kept at 7.5 for 3 hours with stirring. Workup of the reaction mixture yielded the title compound as a syrup.

(E) N-(t-Butyloxycarbonyl)-4-azido-DL-threonine 16.8 grams of N-(t-Butyloxycarbonyl)-4-chloro-DL-threonine was dissolved in 170 ml of methanol and 70 ml of water. The pH was adjusted to 11 by the addition of potassium carbonate (9.5 g). Then 13 g of sodium azide was added and the pH was kept at 11 for 24 hours (room temperature). The methanol was removed in vacuo, and the aqueous phase was layered with ethyl acetate and adjusted to pH 2.5 by the addition of phosphoric acid. The aqueous phase was extracted two additional times with ethyl acetate; the combined organic phases were dried (MgSO4) and evaporated to yield 16.5 grams of the title compound as a syrup.

(F) [[N²-(t-Butyloxycarbonyl)-4-azido-DL-threoninamidoloxylacetic acid, diphenylmethyl ester 16.4 g of N-(t-Butyloxycarbonyl)-4-azido-DL-threonine was dissolved in 250 ml of tetrahydrofuran. To the solution there was added 16.3 g to (aminooxy)acetic acid, diphenylmethyl ester and 40 ml of water, followed by 0.97 g of N-hydroxybenzotriazole and 13.1 g of dicyclohexylcarbodiimide. After stirring overnight, the precipitated dicyclohexylurea was filtered off. The filtrate was evaporated in vacuo, and the oily residue was dissolved in ethyl acetate, filtered and washed with sodium bicarbonate solution and brine. After drying (MgSO4) and evaporation of the solvent in vacuo, 36 grams of crude product were obtained as an oil. The material was purified by chromatography on silica gel, eluting with a 70:30 mixture of dichloromethane/ethyl acetate.

(G) [[N²-(t-Butyloxycarbonyl)-4-azido-O-(methylsulfonyl)-DL-threoninamido]oxy]acetic acid, diphenylmethyl ester 6.5 grams of [[N²-(t-Butyloxycarbonyl)-4-azido-DL-threoninamido]oxy]acetic acid, diphenylmethyl ester were mesylated according to the procedure described in example 39B to yield 6.8 grams of the title compound as an oil.

(H) (trans)-[[4-(Azidomethyl)-3-[(t-butyloxycarbonyl)amino]-2-oxo-1-azetidinyl]oxy]acetic acid, diphenylmethyl ester 6.8 grams of [[N²-(t-Butyloxycarbonyl)-4-azido-O-(methylsulfonyl)-DL-threoninamido]oxy]acetic acid, diphenylmethyl ester were cyclized according to the procedure described in example 39C to yield 3.8 g of the title compound as an oil.

(I) (trans)-[[3-Amino-4-(azidomethyl)-2-oxo-1-azetidinyl]oxy]acetic acid, trifluoroacetate salt 3.8 grams of trans)-[[4-(Azidomethyl)-3-(t-butyloxycarbonyl)amino]-2-oxo-1-azetidinyl]oxy]-acetic acid, diphenylmethyl ester was dissolved in 3 ml of anisole at room temperature and cooled to −10° C. At this temperature, 30 ml of trifluoroacetic acid was added and the mixture was kept at −10° C. for 30 minutes. 70 ml of ether was added and the title compound precipitated (0.6 grams). A second crop of 0.6 grams of product was obtained by evaporation of the filtrate and treatment of the oily residue with ether.

(J) [3S-[3α(Z),4β]]-[[3-[[(2-Amino-4-thiazolyl)-(methoxyimino)acetyl]amino]-4-(azidomethyl) 2-oxo-1-azetidinyl]oxy]acetic acid, potassium salt 0.33 g of (trans)-[[3-Amino 4-(azidomethyl)-2-oxo-1-azetidinyl]oxy]acetic acid, trifluoroacetate salt was suspended in 20 ml of acetonitrile and 0.6 ml N-methyl-N-trimethylsilyltrifluoroacetamide was added to yield a solution after stirring for 30 minutes. The solution was cooled to 0° C. and 0.35 g of (Z)-2-amino-α-(methoxyimino)-4-thiazoleacetic acid N-hydroxybenzotriazole ester was added. The mixture was stirred at room temperature for 2.5 houre. 1 ml of a solution of potassium ethylhexanoate was added and the mixture was evaporated in vacuo to a small volume. On addition of ether, the title compound precipitated yielding 0.55 grams of crude material. The crude product was purified by chromatography on HP-20. The title compound was eluted with water/acetone (80:20), yielding 95 mg of product.

EXAMPLE 89

(trans)-[[3-(t-Butyloxycarbonyl)-4-methyl-2-oxo-1-azetidinyl]oxy](methylthio)acetic acid, methyl ester

(A) Bromo(methylthio)acetic acid, methyl ester 24.0 g of (methylthio)acetic acid, methyl ester, 32.8 g of N-bromosuccinimide and 100 mg of 2,2′-azobis-(2-methylpropionitrile) were heated for 1 hour to 60° C. in 150 ml of carbon tetrachloride. After cooling and filtration, the solvent was removed in vacuo and the residue distilled, yielding 26.8 g of bromo(methylthio)acetic acid, methyl ester as a red oil.

(B) (trans)-[[3-(t-Butyloxycarbonyl)-4-methyl-2-oxo-1-azetidinyl]oxy](methylthio)acetic acid, methyl ester 2.16 g of 3-[(t-Butyloxycarbonyl)amino]-1-hydroxy-4-methyl-2 azetidinone and 2 20 g of bromo(methylthio)acetic acid, methyl ester were dissolved in 50 ml of dlmethylformamide 1.11 g of triethylamine in 30 ml of dimethylformamide was added over a period of 3 hours and the mixture was stirred for 2 days at ambient temperature. The solvent was removed in vacuo and the residue suspended in 20 ml of ethyl acetate. After the ammonium salt was filtered off. The solution was concentrated and chromatographed on silica gel with ethyl acetate as eluent, yielding 2.0 g of product as an oil.

IR (film): 1780, 1745, 1710 cm⁻¹. NMR (DMSO-d₆): δ=1.38(s,9H), 2.22 (s,3H), 3.76 (s,3H), 5.63 and 5.66 (2s, 1H), 7.60 (br, d, 1H).

EXAMPLE 90

[3S-[3α(Z),4β]]-[[3-[[(2-Amino-4-thiazolyl)-methoxyimino)acetyl]amino]-4-methyl-2-oxo-1-azetidinyl]oxy]acetic acid, 1-methylethyl ester

(A) (3S-trans)-3-(t-Butyloxycarbonylamino)-1-hydroxy-4-methyl-2-azetidinone 10.5 g of (3S-trans)-3-(t-Butyloxycarbonylamino)-1-benzyloxy-4-methyl-2-azetidinone was dissolved in 250 ml of methanol and hydrogenated with 1.43 g of palladium on carbon (10%) as the catalyst. After 45 minutes the catalyst was filtered off and the filtrate was evaporated in vacuo. The crystalline title compound was dried (vacuum desiccator) at room temperature yielding 7.3 g of the title compound, melting point 161°–162° C., dec.

(B) (3S-trans)-[[3-[(t-Butyloxycarbonyl)amino]-4-methyl-2-oxo-1-azetidinyl]oxy]acetic acid, 1-methylethyl ester 11.3 g of Triethylamine was dropped into a solution of 19.5 g of (3S-trans)-3-(t-butyloxycarbonylamino)-1-hydroxy -4-methyl-2-azetidinone and 14.8 g of chloroacetic acid, 1-methylethyl ester in 400 ml of dry dimethylformamide. The whole was stirred at room temperature for 3 days. Triethylamine hydrochloride was filtered off and the solvent was stripped at 35° C. in vacuo. The residual oil was taken up in ether, the extract was allowed to stand in the refrigerator for about two hours, filtered and the ether again evaporated in vacuo. The resulting oily title compound (30 g) containing about 2 g of impurities was used in the next step without further purification.

(C) (3S-trans)-[[3-amino-4-methyl-2-oxo-1-azetidinyl]oxy]acetic acid, 1-methylethyl ester, trifluoroacetate 30 g of unpurified (3S-trans)-[[3-[(t-butyloxycarbonyl)amino]-4-methyl-2-oxo-1-azetidinyl]oxy]acetic acid, 1-methylethyl ester was dissolved in a mixture of 230 ml of trifluoroacetic acid and 23 ml of anisole at −10° C. Stirring was continued at −2° C. for 30 minutes. On evaporation of the trifluoroacetic acid solution in vacuo at low temperature (10° to 20° C.) the oily residue was dissolved in 350 ml of anhydrous ether and immediately after that operation the trifluoroacetate salt began to crystallize. Placing the ethereal mixture into the refrigerator increased the yield. After filtering off, the title compound was washed twice with anhydrous ether and finally with petroleum ether (40°–60° C.) to give, on desiccator drying (P₂O₅), 18 g of product, melting point 125.5° C.

(D)

[3S-[3α(Z),4β]]-[[3-[[(2-Amino-4-thiazolyl)-(methoxyimino)acetyl]amino]-4-methyl-2-oxo-1-azetidinyl]oxy]acetic acid, 1-methylethyl ester While stirring, 5.8 g of anhydrous triethylamine dissolved in 50 ml of anhydrous dimethylformamide was added dropwise to a solution of 17.5 g (3S-trans)-[[3-amino-4-methyl-2-oxo-1-azetidinyl]oxy]acetic acid, 1-methylethyl ester, trifluoroacetate (0.053 mol) and 16.9 g of (Z)-2-amino-α-methoxyimino)-4-thiazoleacetic acid, 1-hydroxybenzotriazole ester (0.053 mol) in 200 ml of dimethylformamide cooled down to 0° C. After two hours (when triethylamine addition was completed) the temperature of the reaction mixture was allowed to increase slowly to 20° C. Stirring at that temperature was continued for an additional 4 hours. Dimethylformamide was removed in vacuo, the residual oil, taken up in ethyl acetate, was shaken with ice-cold aqueous sodium bicarbonate (1N) and subsequently with ice-cold water. The ethyl acetate layer which was dried with NaSO₄ was evaporated in vacuo to give 18.8 g of the title compound. Chromatography on silica gel with tetrahydrofuran/ethyl acetate (1:1) have a pure product, melting point 87°–95° C. dec.

EXAMPLE 91

[3S-[3α(Z),4β]]-[[3-[[(2-Amino-4-thiazolyl)-(methoxylimino)acetyl]amino]-4-methyl-2-oxo-1-azetidinyl]oxy]acetic acid, 2-propenyl ester (A)

(3S-trans)-[[3-[(t-Butyloxycarbonyl)amino]-2-methyl-4-oxo-1-azetidinyl]oxy]acetic acid, 2-propenyl ester To a solution of 17.3 g of (3S-trans)-3-(t-butyloxycarbonylamino)-1-hydroxy-4-methyl-2-azetidinone and 12.9 g of chloroacetic acid, 2-propenyl ester in 350 ml of dry dimethylformamide. The mixture was allowed to stand for 4 days at room temperature and subsequently worked up as described in Example 90B. Yield 25.5 g of crude ester.

(B)

(3S-trans)-[[3-amino-4-methyl-2-oxo-1-azetidinyl]oxy]acetic]acid, 2-propenyl ester, trifluoroacetate 25.5 g of the crude (3S-trans)-[[3[(t-butyloxycarbonyl)amino]-4-methyl-2-oxo-1-azetidinyl]oxy]acetic acid, 2-propenyl ester was added to a stirred mixture of 200 ml of trifluoroacetic acid and 20 ml of anisole cooled to −10° C. After allowing to react at −2° C. for 25 minutes, excess trifluoroacetic acid was removed in vacuo at low temperature, varying from 20° to 25° C. The oily residue was taken up in 250 ml of anhydrous ether and kept in the refrigerator. The crystallized title compound was filtered off, washed twice with anhydrous ether, finally with petroleum ether (40°–60° C.) and dried in the desiccator over P₂O₅ to give 17.7 g of product, melting point 112°–113° C.

(C) [3S-3α(Z),4β]]-[[3-[[(2-Amino-4-thiazolyl)-(methoxyimino)acetyl]amino]-4-methyl-2-oxo-1-azetidinyl]oxy]acetic acid, 2-propenyl ester To a stirred mixture of 17.4 g of (3S-trans)[[3-amino 4 methyl-2-oxo-1-azetidinyl]oxy]acetic acid, 2-propenyl ester, trifluoroacetate (0.053 mol) and 16.9 g of (Z)-2-amino-α-methoxyimino)-4-thiazoleacetic acid 1-hydroxybenzotriazole ester in 200 ml of dimethylformamide cooled to 0° C. was added portionwise 5.8 g of triethylamine in 40 ml of anhydrous dimethylformamide. Then temperature of the solution was kept at 5° C. for one hour, subsequently at 10° C. for two hours and allowed to stand overnight at room temperature. Work up was made in the manner of example 90D. Yield 18 g; melting point 75°–80° C. dec.

EXAMPLE 92

[3S-[3α(Z),4β]]-[[3-[[(2-Amino-4-thiazolyl)-(methoxylmino)acetyl amino 4-methyl-2-oxo-1azetdinyl1oxy]acetic]acid, 2-propynyl ester (A)

(3S-trans)-[[3-[(t-Butyloxycarbonyl)amino]-4-methyl-2-oxo-1 azetidinyl]oxy]acetic acid, 2-propynyl ester Following the procedure of Example 91A, but substituting chloroacetic acid 2-propynyl ester (1.7 g) for chloroacetic acid, 2-propenyl ester yielded 2.2 g of the title compound as an oil, which was used in the next step without purification.

(B)

(3S-trans)-[[3-amino-4-methyl-2-oxo-1-azetidinyl]oxy]acetic acid, 2-propynyl ester, trifluoroacetate Deprotection of the preceding oil (2.2 g) was achieved by trifluoroacetic acid/anisol (25 ml/2.5 ml) using the procedure of example 92B. Yield 1.7 g; melting point 106°–107° C.

(C)

[3S-[3α(Z),4β]]-[[3-[[(2-Amino-4-thiazolyl)-(methoxyimino)acetyl]amino]-4 methyl-2-oxo-1azetidinyloxy]oxy]acetic acid, 2-propynyl ester 1.6 g of (3S-trans)-[[3-amino-4-methyl2-oxo-1-azetidinyl]oxy]acetic acid, 2-propynyl ester, trifluoroacetate was coupled with 1.6 g of (Z)-2-amino-α-methoxyimino)-α-thiazoleacetic acid. 1-hydroxybenzotriazole ester as described in example 92° C. Chromatography on silica gel with tetrahydrofuran/ether (1:1) yielded 1.1 g of the title compound melting point 69°–75° C. dec.

EXAMPLE 93

3S-[3α(Z),4β]]-[[3-[[(2-Amino-4-thiazolyl)-methoxyimino)acetyl]amino]-4-methyl-2-oxo-1azetidinyl]oxy]acetic acid, propyl ester (A)

(3S-trans)-[[3-[(t-Butyloxycarbonyl)amino]-4-methyl-2-oxo-1-azetidinyl]oxy]acetic acid, propyl ester Following the procedure of example 91A, but substituting chloroacetic acid, propyl ester (3.0 g) for chloroacetic acid, 2-propenyl ester yielded 4.2 g of the title compound; melting point 72 20 C.

(B)
(3S-trans)-[[3-amino-4-methyl-2-oxo-1-azetidinyl]oxy]acetic acid, propyl ester, trifluoroacetate Treatment of the foregoing ester (4.2 g) with 50 ml of trifluoroacetic acid and 5 ml anisole according to Example 91B yielded 3.3 g of the title compound.

(C) 3S-[3α(Z),4β]]-[[3-[2-Amino-4-thiazolyl)-methoxyimino)acetyl]amino]-4-methyl-2-oxo-1azetidinyl]oxy]acetic acid, propyl ester 4.88 ml of MSTFA (95%) (2.5 mmol) was added to a suspension of 3.39 of (3S-trans)-[[3-amino-4-methyl-2-oxo-1-azetidinyl]oxy lacetic acid, propyl ester, trifluoroacetate in 60 ml dry acetonitrile at 0° C. Stirring was continued until the trifluoroacetate was dissolved. The clear solution was allowed to stand overnight. After evaporation of acetonitrile in vacuo the residual oil (3.39 g) was dissolved in 40 ml of dry tetrahydrofuran, 2.96 g of (Z)-2-amino-α-methoxyimino)-4-thiazoleacetic acid. 1-hydroxybenzotriazole ester (8.44 mmol) was added and the mixture was stirred for 4 hours at room temperature. The solvent was stripped in vacuo at 30° C., and the residue was taken up in ethyl acetate, shaken with ice-cold aqueous sodium bicarbonate (1N) and subsequently with ice water. The ethyl acetate layer was dried with $Na_2SO_4$ and the title compound (4 g oil) chromatographed on silica gel with ethy 1 acetate. Yield 3.1 g; melting point 68°-71° C. dec.

EXAMPLE 94

[3S-[3α(Z),4β]]-[[3-[[(2-Amino-4-thiazolyl)-methoxyimino)acetyl]amino]-4-methyl-2-oxo-1-azetidinyl]oxy]acetic acid, 2-chloroethyl ester (A)
(3S-trans)-[[3-[(t-Butyloxycarbonyl)amino]-4-methyl-2-oxo-1-azetidinyl]oxy]acetic acid, 2-chloroethyl ester Following the procedure of example 91A, but substituting chloroacetic acid, 2-chloroethylester (4.32 g) for chloroacetic acid. 2-propenylester yielded 5.2 g of he title compound (ethyl acetate/ether 1:1 was used as the eluent for chromatography on silica gel).

(B)
(3S-trans-[[3-Amino-2-methyl-4-oxo-1-azetidinyl]oxy]acetic acid, 2-chloroethyl ester, trifluoroacetate Using trifluoroacetic acid and anisole (as described in example 91B) the title compound was prepared from the preceding t-butyloxycarbonyl protected amino derivative. Yield 4.19 g.

(C)
[2S-[2α,3β(Z)]]-[[3-[[(2-Amino-4-thiazolyl)-(methoxyimino)acetyl]amino]-2-methyl4-oxo-1azetidinyl]oxy]acetic]acid, 2-chloroethyl ester 2.0 g of (3S-trans-[[3-Amino-4-methyl-2 oxo-1-azetidinyl]oxy]acetic acid, 2-chloroethyl ester, trifluoroacetate was coupled with 1.89 g of (Z)-2-amino-α-methoxyimino)-4-thiazoleacetic acid. 1-hydroxybenzotriazole in the manner described in Example 91C to give 1.66 g of the title compound (tetrahydrofuran/ether 1:1 was used as the eluent for chromatography on silica gel); melting point 84°-85° C. dec.

EXAMPLE 95

[3S-13α(Z),4β]]-[[3-[[(2-Amino-4-thiazolyl)methoxyamino)acetyl]amino]-4-methyl-2-oxo-1-azetidinyl]oxy]acetic acid, cyclohexyl ester (3S-trans)-[[3-[(t-Butyloxycarbonyl)amino]-4-methyl-2-oxo-1-azetidinyl]oxy]acetic acid. cyclohexyl ester (2.23 g) prepared analogously to the procedure of example 91A was dissolved in a solution of 25 ml of trifluoroacetic acid and 2.5 ml of anisole at −10° C. The mixture was evaporated in vacuo 25 minutes later and the residue was stirred with ether, filtered off and dried over $P_2O_5$ to give colorless crystals of (3S)-[[3-amino-4 methyl-2-oxo-1-azetidinyl]oxy]acetic acid, cyclohexyl ester, trifluoroacetate salt (yield 1.53). The salt (1.50 g) was suspended in 30 ml of acetonitrile. MSTFA (2.37 ml) was added at 0° C. and the solution was allowed to stand overnight. After evaporating in vacuo, the residue (1.75 g) was dissolved in dry tetrahydrofuran (25 ml), 1.4 g of (Z)-2-amino-α-methoxyimino)-4-thiazoleacetic acid, 1-hydroxybenzotriazole ester was added and the mixture was stirred at room temperature for 4 hours. Tetrahydrofuran was removed in vacuo at 30° C., the residue was taken up in ether, shaken with ice-cold aqueous $NaHCO_3$ (in) and twice with cold water. The dried ethyl acetate layer was evaporated in vacuo. The resulting oil (2.14 g) chromatographed on silica gel with ethyl acetate to give 1.58 g of the title compound; melting point 85°-90° C. dec.

EXAMPLE 96

[3S-[3α(Z),4β]]-[[3-[[(2-Amino-4-thiazolyl)-(methoxyimino)acetyl]amino]-4-methyl-2-oxo-1azetidinyl]oxy]acetic acid, cyclopentyl ester Following the procedure of Example 95, but substituting (3S-trans)-[[3-[(t-butyloxycarbonyl)-amino-4-methyl 2-oxo-1-azetidinyl]oxy]acetic acid, cyclopentyl ester for (3S-trans)-[3-[(t-butyloxycarbonyl)amino]-4-methy 1-2-oxo-1-azetidinyl]oxy]acetic acid, cyclohexyl ester yielded the title compound; melting point 90°-95° C., dec.

EXAMPLE 97

[3S-[α(Z),4β]]-[[3-[[(2-Amino-4-thiazolyl)-methoxyimino)ace (methoxyimino)acetyl]amino]-4-methyl-2-oxo-1-azetidinyloxy]acetic acid, cyclonentylmethyl ester (3S-trans)-[[3-[(t-Butyloxycarbonyl)amino]-4-methyl-2-oxo-1-azetidinyl]oxy]acetic acid, cyclopentylmethylester accessible from (3S-trans)-3(-t-butyloxycarbonylamino-1-hydroxy-4-methyl-2-azetidinone and chloroacetic acid, cyclopentylmethyl ester was deprotected and coupled to the title compound following the procedure described in Example 90B to 90D; melting point 73°-80° C., dec.

EXAMPLE 98

[3S-[3α(Z),4β]]-[[-[[(2-Amino-4-thiazolyl)-methoxyimino)acetyl]amino]-4-methyl-2-oxo-1-azetidinyl]oxy]acetic acid, 2,2-dimethyprooyl ester (3S-trans)-[[3-[(t-Butyloxycarbonyl)amino]-4-methyl-2-oxo-1-azetidinyl]oxy]acetic acid. 2,2-dimethylpropyl ester was converted via the corresponding trifluoroacetate salt to the title compound (melting point 74°-76° C., dec.) utilizing the procedure of example 91A to 91C.

EXAMPLE 99

[3S-[3α(Z),4β]]-[[3-]](2-Amino-4thiazolyl)-(methoxyimino)acetyl]amino]-4-methyl-2-oxo-1azetidinyl]oxy]acetic acid, 2-ethylbutyl ester Following the procedure of Example 91A to 91C, (3S-trans)-[[3-[(t-Butyloxycarbonyl)amino]-4-methyl-2-oxo-1-azetidinyl]oxy]acetic acid, 2-ethylbutyl ester was converted via the trifluoroacetate salt to the title ester; melting point 56°-60° C., dec.

EXAMPLE 100

[3S-[3α(Z),4β]]-[[3-[[(2-Amino-4-thiazolyl)-methoxyimino)acetyl]amino]-4-methyl-2-oxo-1-azetidinyl]oxy]acetic acid. 2,2,2,-trifluoroethyl ester Following the procedure of Example 90 (3S-trans)-[[3-[(t-Butyloxycarbonyl)amino]-4-methyl-2-oxo1-azetidinyl]oxy]acetic acid. 2,2,2-trifluoro-ethyl ester was deacylated to its trifluoroacetate salt and subsequently coupled with (Z)-2-amino-α-methoxyimino)-4-thiazoleacetic acid, 1-hydroxy-benzotriazole ester to give the title compound; melting point 75°-81° C., dec.

EXAMPLE 101

3S-[3α(Z),4β]]-[[3-[[(5-Amino-1,2,4-thiadiazol-3-yl) methoxyimino)acetyl]amino]-4-methyl-2-oxo-1-azetidinyl]oxy]acetic acid.

(3S-trans)-[[3-[(Butyloxycarbonyl)amino]-4-methyl-2-oxo-1-azetidinyl]oxy]acetic acid, diphenylmethyl ester (15 g; 34 mmol) was dissolved in a solution of 112 ml of trifluoroacetic acid and 11.2 ml of anisole at −10° C. The mixture was evaporated in vacuo 10 minutes later and the residue was stirred with ether, filtered off and dried over $P_2O_5$ to give 7.3 g crystals of (3S)-[[3-amino-4-methyl-2-oxo-1 azetidinyl]oxy]acetic acid, trifluoroacetate salt. The salt (7.3 g) was suspended in 30 ml of dry acetonitrile, MSTFA (3.34 ml) was added and stirring was continued for 1 hour. After evaporating in vacuo the residue was dissolved in dry tetrahydrofuran, (Z)-5-amino-1,2,4-thiadiazoI-3 yl-α- meythoxyimino)acetic acid. 1-hydroxybenzotriazole ester (2.0 g) was added, and the mixture was stirred overnight at room temperature and evaporated in vacuo. After adding ether the crude silylated product was decomposed with 0.5 ml methanol. The undissolved product was filtered off, dissolved in tetrahydrofuran and chromatographed on silica gel with ethyl acetate/ether 1:1 to give the title compound; melting point 165°-166° C.

EXAMPLE 102

[3S-[3α(Z),4β]]-[[3-[[(5-Amino-1,2,4-thiadiazol-3yl)-(methoxyimino)acetyl]amino]-4-methyl-2-oxo-1-azetidinyloxylacetic acid, 1-methylethyl ester 1.35 g of (3S-trans)[[3-amino-4-methyl-2-oxo1-azetidinyl]oxy]acetic acid, 1-methylethyl ester, trifuoroacetate (4.1 mmol) was suspended in 25 ml of dry acetonitrile. MSTFA (2.28 ml) was added at 0° C., stirring was continued for 30 minutes and the solution left overnight at room temperature. After evaporating in vacuo the residue (1.92 g) was dissolved in 13 ml of dry tetrahydrofuran. (Z)-5-amino-1,2,4-thiadiazol-3-yl-α-(methoxyimino)acetic acid, 1-hydroxybenzotriazole ester (1.75 g) was added, the mixture stirred overnight at room temperature and evaporated in vacuo. The residue was taken up in ethyl acetate. shaken with ice-cold aqueous $NaHCO_3$ (1N) and then with ice water. The ethyl acetate layer was dried with $Na_2SO_4$ and chromatographed on silica gel using ethyl acetate as the eluent. Yield of the title compound was 1.10 g, melting point 83°-85° C.

EXAMPLE 103

[3S [3α(Z),4β]]-[[3-[[(6-Amino-2-pyridinyl)(methoxyimino)acetyl]amino]4-methyl-2-oxo-1azetidinyl]oxy]acetic acid, monosodium salt Following the procedure of Example 101, but substituting (Z)-6-amino-2-pyridinyl-α-methoxyimino)acetic acid. 1-hydroxybenzotriazole ester for (Z)-5-amino-1,2,4-thiazol-3-yl-mmethoXyimino acetic acid. 1-hydroxybenzotriazole ester yielded the free acid of the title compound. It was suspended in ice cold water. The pH was adjusted to 6.5 with 1N sodium hydroxide and the clear solution was freeze-dried to give the salt; melting point 140° C. dec.

Example 104

(3S-trans)-[[3-[[[(2.6-Dichloro-4-pyridinyl)thiojacetyl]amino]-4-methyl-2-oxo-1-azetidinyl]oxy]acetic acid, monosodium salt Following the procedure of Example 103, but substituting 2,6-dichloro-4-pyridinylthioacetic acid. 4-nitrophenylester for (Z)-6-amino-2- pyridinyl-α-(methoxyimino)acetic acid, 1-hydroxybenzotriazole ester yielded the title compound, melting point 97°-100° C. dec.

EXAMPLE 105

[3S-[3α(Z),4β]]-[[3-[[(2-Amino-4-thiazolyl)methoxy mino)acetyl]amino]-4-methyl-2-oxo-1-azetidinyl]oxy]acetic acid. 1-[[(cyclohexyloxy)carbonyl]oxy]ethoxy ester

[3S-[3α(Z),4β]]-[[3-[[(2-Amino-4-thiazolyl)methoxyimino)acetyl]amino]-4-methyl-2-oxo-azetidinyl]oxy]acetic acid, monopotassium salt (0.40 g) was dissolved in 10 ml of dry dimethylformamide. α-Chloroethyl-cyclopentylcarbonate (0.20g) and 0.083g of potassium iodide were added at room temperature and the mixture was stirred at room temperature for 2 days. The solvent was evaporated in vacuo and the residue was taken up in ethyl acetate, washed successively with water, 1N $NaHCO_3$ solution, water and then dried ($Na_2SO_4$). After removal of the solvent in vacuo. The resulting oil (0.34 g) was purified by chromatography on silica gel with a mixture of tetrahydrofuran ether (1:1) as eluent to give 0.31 g oily title compound, which after treatment with water crystallized, melting point 85°-90° C. dec.

Example 106

[3S-[3α(Z),4β]]-[[3-[[(2-Amino-4-thiazolyl)(methoxyimino)acetyl]amino]-4-methyl-2-oxo-1azetidinyl]oxy]acetic acid. 1-[(ethoxycarbonyl)oxy1ethyl ester Following the procedure of Example 105. but substituting α-iodoethyl-ethylcarbonate for α-chloroethyl cyclopentylcarbonate yielded the title compound. melting point 120°-125° C. dec.

EXAMPLE 107

[3S-[3α(Z),4β]]-[[[[3-[[(2-Amino-4-thiazolyl)methoxyimino)acetyl]amino]-4-methyl-2-oxo-1azetidinyl]oxy]acetyl]oxy]acetic acid, 1,1-dimethylethyl ester To a solution of [3S-[3α(Z),4β-]]-[[3-]](2-amino-4-thoazolyl)(methoxyimino)acetyl]amino]-methyl-2-oxo-1-azetidinyl]oxy]acetic acid, sodium salt in 50 ml of dry dimethylformamide was added dropwise 4.14g of t-butyl iodoacetate. Stirring was continued at room temperature for 3 hours. The solvent was evaporated in vacuo at room temperature, and the residue was taken up in ethyl acetate, washed successively with ice-cold water, ice-cold aqueous NaHCO3 solution and ice-cold brine, and dried over CaSO4. After filtration and removal of the solvent in vacuo, the residue was chromatographed on silica gel eluting with ethyl acetate, yielding 2.9 g of the title compound, melting point 77° C. dec.

EXAMPLE 108

[3S[3α(Z),4α-]]-[[3-[[(2-Amino-4-thiazolyl)-methoxyimino)acetyl]amino]-4-methyl-2-oxo-1-azetidinyl]oxy]acetic acid, monosodium salt A solution of 0.33 g of triethylamine in 5 ml of dry dimethylformamide was dropped into a solution of 0.33 g of (3S-cis)-[(3-amino-4-methyl-2oxo-1-azetldinyl)oxy]acetic acid, trifluoroacetate salt and 0.35 g of (Z)-2-amino-2-(methoxyimino)-4-thiazoleacetic acid, 1-hydroxy-benzotriazole ester in 20 ml of dimethylformamide at 0° C. and stirring was continued for 3 hours at room temperature. The solvent was evaporated in vacuo. The residue was suspended in 10 ml of n-butanol and a solution of 0.55 g of sodium 2-ethyl-hexanoate in 10 ml n-butanol was added. The mixture was stirred for 4 hours at room temperature. The precipitate was collected by suction. washed with n-butanol and ether and then dried in vacuo over P2O5. After reverse phase chromatography on resin HP-20 eluting with water and freeze drying of the appropriate fractions. The title compound was obtained: yield 0.14 g. dec. >170° C.

EXAMPLE 109

[3S-[3α(Z),4α]]-2-[[[1-(2-Amino-1-thiazolyl)-2-[[1-(carboxymethoxy)-4-methyl-2-oxo-3-azetidinyl]-amino]-2-oxoethylidene]amino]oxy]-2-methylpropanoic acid, disodium salt (A) [3S-[3α(Z),4α]]-2-[[[1-(2-Amino-4-thiazolyl)-2-[[1-(carboxymethoxy)-4-methyl-2-oxo-3-azetidinyl]amino]-2-oxoethylidene]amino]oxy]-2-methylpropanoic acid, diphenylmethyl ester, monosodium salt 1.3 ml of MSTFA was added to a suspension of 0.63 g of (3S-cis)-[(3-amino-4-methyl2-oxo-1-azetidinyl)oxy]acetic acid, trifluoroacetate salt in 10 ml of dry acetonitrile at 0° C. and stirring was continued for 30 minutes at room temperature. After evaporating in vacuo the residue was dissolved in 15 ml of dry tetrahydrofuran and this solution was added at 0° C. to a mixture of 0.97 g of (Z)-2-amino-α-[[2-(diphenylmethoxy-1,1-dimethyl-1,1-dimethyl-2-oxoethoxy]imino]-4-thiazoleacetic acid, 0.34 g of 1-hydroxybenzotriazole and 0.45 g of dicyclohexylcarbodiimide in 10 ml of tetrahydrofuran which had been reacting for 2 hours at 50° C. After stirring overnight at room temperature, the precipitate was evaporated in vacuo. Ice-cold water and ether were added to the residue and the pH was adjusted to 6.5 with 5% sodium bicarbonate solution. The organic layer and insoluble products were separated and the aqueous phase was freeze-dried. Column chromatography on HP-20 resin eluting with water and water/acetone (7:3) yielded pure product; 0.56 g, melting point >168° C., dec.

(B)
[3S-[3α(Z),4α]]-2-[[[1-(2-Amino-4-thiazolyl(-2-[[1-(carboxymethoxy)-4-methyl-2-oxo-3-azetidinyl]amino]-2-oxoethylidene]imino]oxy]-2-methylpropanoic acid, disodium salt 0.29 g (0.47 mmol) of freeze-dried [3S-[3α(Z),4α]]-2-[[[1-(2-amino-4-thiazolyl)-2-[[1-(carboxymethoxy)-4-methyl-2-oxo-3-azetidinyl]-amino]-2-oxoethylidene]amino]oxy]-2-methylpropanoic acid, diphenylmethyl ester, monosodium salt was suspended in a solution of 2.1 ml of trifluoroacetic acid and 0.21 ml anisole at −10° C. After stirring for 10 minutes at 0° C. the trifluoroacetic acid was removed in vacuo (bath temperature ≦5° C.). Ether and ice-cold water were added and the pH was adjusted to 6.5 by means of 5% sodium bicarbonate. After freeze drying of the aqueous layer the crude product was chromatographed on HP-20 eluting with water: yield 0.16 g, dec. >60° C.

EXAMPLE 110

[3S-[3α(Z),4β]]-[[3-[[(2-Amino-4-thiazolyl)-methoxyimino)acetyl]amino]-4-methyl-2-oxo-1-azetidinyl]oxy]acetic acid, [(3-pentyloxy)carbonyl]methyl ester (A) Bromoacetic acid, [(3-pentyloxy)carbonyl]-methyl ester Bromoacetic acid, 3-pentyl ester (330 g, 1.6 mole) was dissolved in 300 ml of dimethylformamide. Bromoacetic acid, potassium salt (142 g) was added portionwise with stirring and the mixture was stirred overnight. It was then poured into 1 liter of ice-cold water and 500 ml of ether was added. After washing with water, NaHCO3 solution and drying with MgSO4, the ether was evaporated. On distillation 156 g of the starting ester was recovered and 103.5 g of the title compound (boiling point 160°–162° C. at 12 mm of Hg) was obtained.

(B)
(3S-trans)-[[3-[(t-Butyloxycarbonyl)amino]-4-methyl-2-oxo-1-azetidinyl]oxy]acetic acid, [(3-pentyloxy)carbonyl]methyl ester (3S-trans)-3-[(t-Butyloxycarbonyl)amino]-1-hydroxy-4-methyl-2-azetidinone (21.6 g) was dissolved in 250 ml of dimethylformamide. At 0° C. 26.7 g of bromoacetic acid. [(3-pentyloxy)carbonyl]-methyl ester was added, followed by 17 ml of triethylamine. The mixture was stirred overnight, and the dimethylformamide was evaporated in vacuo. The oily residue was dissolved in 300 ml of ethyl acetate, washed with ice-cold NaHCO3 solution and then washed three times with ice water. After drying over MgSO4, the solvent was evaporated in vacuo yielding 35.6 g of the title compound as an oil.

. (C)
(3S-trans)-[(3-Amino-4-methyl-2-oxo-1azetidinyl)oxy]acetic acid, [(3-pentyloxy)-carbonyl]methyl ester (3S-trans1-[[3-[(t-Butyloxycarbonyl)amino]-4-methyl2-oxo-1-azetidinyl]oxy]acetic acid, [(3pentyloxy)carbonyl]methyl ester was dissolved in dichloromethane. At −10° C., 50 ml of trifluoroacetic acid was slowly added. The temperature was maintained at −10° C. for 20 minutes and the solvent was evaporated in vacuo to yield 13 g of the title compound as an oil.

(D) [3S-[3α(Z), 4β]]-[[3-[[(2Amino-4thiazolyl)-(methoxyimino)acetyl]amino]-4-methyl-2-oxo-1-azetidinyl]oxy]acetic acid, [(3-pentyloxy)-carbonyl]methyl ester (Z)-2-Amino-α-(methoxyimino)-4-thiazole-acetic acid (6g) was dissolved in 100 ml of dimethylformamide. 5 ml of triethylamine was added, and, after cooling to −25° C. 6.2 ml of diphenyl phosphochloridate was added. The mixture was stirred at −25° C. for 50 minutes and then added to a solution prepared from 13 g of (3S-trans)-[(3-amino-4-methyl-2 oxo-1-azetidinyl)oxy]acetic acid. [(3-pentyloxy)carbonyl]methyl ester. 21 ml of triethylamine and 100 ml of dimethylformamide at −25° C. The reaction mixture was stirred at −25° C. for 2.5 hours. The solvent was evaporated in vacuo, the residue dissolved in 400 ml of ethyl acetate, washed with ice water. NaHCO$_3$ solution and ice water, dried (MgSO$_4$) and evaporated again to yield the title compound as a solid foam, which was treated with hexane. The yield was 8.7 grams of product, purity 83% (HPLC); melting point 76–80° C.

EXAMPLE 111

[3S-[3α(Z),4β]]-[3 [[(2-Amino-4-thiazolyl)(methoxyimino)acetyl]amino]-4-methyl 2-oxo-1-azetidinyl]oxy]acetic acid, 1-[(3-pentyloxy)-carbonyl]ethyl ester

(A) L-Lactic acid, 3-pentyl ester

A mixture of 180 g of L-lactic acid, 528 g of 3-pentanol and 1 ml of conc. H$_2$SO$_4$ was refluxed in a Dean-Stark apparatus, until no more water formed (ca. 3 hours). The mixture was washed with water, NaHCO$_3$ solution and brine, dried (MgSO$_4$) and distilled to yield the title compound, boiling point 79°–81° C. at 15 mm of Hg.

(B) L-Bromoacetic acid, 1-[(3-pentyloxy)carbonyl]-ethyl ester

L-lactic acid. 3-pentyl ester (47 g) was dissolved in 150 ml of ether. Then 36.6 ml of dimethylphenylamine were added and the mixture was cooled to −10° C. followed by the addition of 53 g of bromoacetyl bromide. The temperature was kept below 5° C. and the mixture was stirred for several hours at room temperature. The reaction mixture was poured into 500 ml of ice water and the organic phase was washed with 2 NH$_3$PO$_4$ solution, NaHCO$_3$ solution and water, dried (MgSO$_4$) and the solvent evaporated. The residue was fractionated in vacuo to yield the title compound as a colorless liquid, boiling point 146°–148° C. at 15mm of Hg.

(C) [3S-[3α(Z),4β]]-[[3-[[(2-Amino-4-thiazolyl)-methoxyimino)acetyl]amino]-4-methyl-2-oxo-1-azetidinyl]oxy]acetic acid, 1-[(3-pentyloxy)-carbonyl]ethyl]ester Following the procedure of Example 110, parts b, c, and d, but utilizing L-bromoacetic acid. 1-[(3-pentyloxy)carbonyl]ethyl ester yielded the title compound.

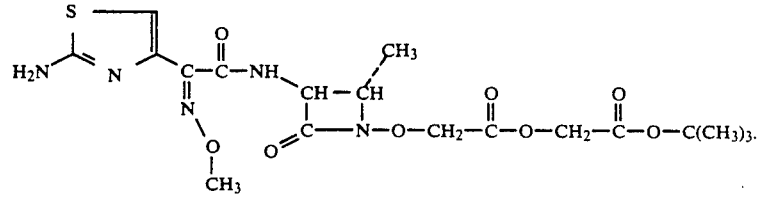

What is claimed is:

1. A 2-azetidinone having an

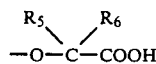

substituent in the 1-position and an acylamino substituent in the 3-position wherein the acyl portion of the group is derived from a carboxylic acid, or an ester or pharmaceutically acceptable salt thereof; wherein $R_5$ and $R_6$ are the same or different and each is hydrogen, alkyl, alkenyl, alkynyl, phenyl, substituted phenyl, cycloalkyl or a 4,5, 6 or 7-membered heterocycle, or $R_5$ and $R_6$ together with the carbon atom to which they are attached are cycloalkyl or a 4,5,6 or 7-membered heterocycle, or one of $R_5$ and $R_6$ is hydrogen and the other is azido, halomethyl, dihalomethyl, trihalomethyl, halogen, alkoxycarbonyl, alkenyl, alkynkyl, 2-phenylethenyl, 2-phenylethynyl, carboxyl, —CH$_2$—X$_1$,

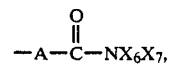

wherein X$_1$ is azido, amino, hydroxy, alkanoylamino, phenylcarbonylamino, (substituted phenyl)carbonylamino, alkysulfonyloxy, phenylsulfonyloxy, (substituted phenyl)-sulfonyloxy, phenyl, substituted phenyl, cyano,

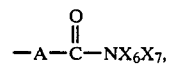

—S—X$_2$, or —O—X$_2$; X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)-carbonyl, or heteroarylcarbonyl; A is —CH═CH—, —(CH$_2$)$_n$—, —CH$_2$—O—, —CH$_2$—NH—, or —CH$_2$—S—CH$_2$)$_n$— is 1, or 2; and X$_6$ and X$_7$ are the same or different and each is hydrogen, alkyl, phenyl, or substituted phenyl, or X$_6$ is hydrogen and X$_7$ is amino, substituted amino, acylamino or alkyoxy, or X$_6$ and X$_7$ when taken together with the nitrogen atom to which they are attached form a 4, 5, 6 or 7-membered heterocycle, wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "substituted phenyl" refers to phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the term "substituted alkyl" refers to alkyl groups substituted with one or more azido, amino, halogen, hydroxy, carboxy, cyano, alkoxycarbonyl, aminocarbonyl alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyhl, thiadiazolyl, pyrimidinyl oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, azetinyl, oxetanyltietanyl, piperidinyl, piperazinyl, imidazoliddinyl, oxazolidinyl, pyrrolidinyl, tetrahyrdopyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms alkylsulfofnyl, phenyl, substituted phenyl, 2-furfurylideneimino, bengylideneiminio or substituted alkyl, wherein the alky group has 1 to 4 carbon atoms, groups; and the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino.

2. A 2-azetedinone in accordance with claim 1 wherein $R_5$ and $R_6$ are each hydrogen.

3. A 2-azetidinone having the formula

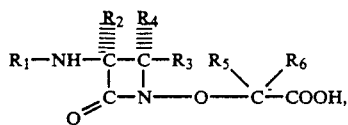

or an ester or pharmaceutically acceptable salt thereof, wherein $R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, $-CH_2X_1$, carboxyl, $-S-X_2$, $-O-X_2$,

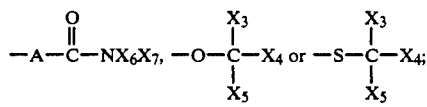

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

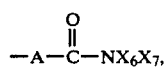

$-S-X_2$ or $-O-X_2$; $X_2$ is alkyl, substituted alkyl, phenyl, substituted phenyl, phenylalkyl, (substituted phenyl)alkyl, alkanoyl, phenylalkanoly, (substituted phenyl)-alkanoyl, phenylcarbonyl, (substituted phenyl)-carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is $-CH=CH-$, $-(CH_2)_n-$, $-CH_2O-$, $-CH_2-NH-$ or $-CH_2-S-CH_2$; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle;

$R_5$ and $R_6$ are the same or different and each is hydrogen, alkyl, alkenyul, alkynyl, phenyl, substituted phenyl, cycloalky or 4, 5, 6 or 7-membered heterocycle, or $R_5$ and $R_6$ together with the carbon atom to which they are attached are cycloalkyl or a 4, 5, 6 or 7-membered heterocycle, or one of $R_5$ and $R_6$ is hydrogen and the other is azido, halomethyl, dihalomethyl, trihalomethyl, halogen, alkoxycarbonyl, alkenyl, alkynyl, 2-phenylethenyl, 2-phenylethynyl, carboxyl, $-CH_2-X_1$, $-S-X_2$, $-O-X_2$, or

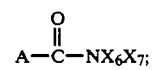

wherein the terms "alkyl" and "alkoxy" refer to groups having 1 to 10 carbon atoms;
the term "cycloalkyl" refers to groups having 3, 4, 5, 6 or 7 carbon atoms;
the terms "alkanoyl", "alkenyl", and "alkynyl" refer to groups having 2 to 10 carbon atoms;
the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;
the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted pheny)thio, alkylsulfinyl or alkylsulfonyl groups;
the term "heteroaryl" refers to pyridinyl, furanyl, pyrrolyl, thienyl, 1,2,3-thiazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;
the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneimino, benzylideneimino or substituted alkyl, wherein the alkyl group has 1 to 4 carbon atoms, groups; and the term "substituted amino" refers to a group having the formula —$NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano alkoxy, phenylalkoxy or amino.

4. A 2-azetidinone in accordance with claim 3 wherein $R_2$ is hydrogen.

5. A 2-azetidinone in accordance with claim 4 wherein $R_3$ and $R_4$ are each hydrogen.

6. A 2-azetidinone in accordance with claim 4 wherein $R_3$ is hydrogen and $R_4$ is methyl.

7. A 2-azetidinone in accordance with claim 4 wherein $R_3$ is methyl and $R_4$ is hydrogen.

8. A 2-azetidinone in accordance with claim 4 wherein $R_5$ and $R_6$ are each hydrogen.

9. A 2-azetidinone in accordance with claim 4 wherein $R_5$ and $R_6$ are each methyl.

10. A 2-azetidinone in accordance with claim 4 wherein $R_1$ is (Z)-[(2-amino-4thiazolyl) (methoxyimino)acetyl].

11. A 2-azetidinone in accordance with claim 3 wherein $R_2$, $R_3$, $R_4$, $R_5$, and $R_6$ are each hydrogen.

12. A 2-azetidinone in accordance with claim 3 wherein $R_2$, $R_3$, $R_5$ and $R_6$ are each hydrogen and $R_4$ is methyl.

13. A 2-azetidinone in accordance with claim 3 wherein $R_2$, $R_4$, $R_5$ and $R_6$ are each hydrogen and $R_3$ is methyl.

14. A 2-azetidinone in accordance with claim 3 wherein $R_1$ is

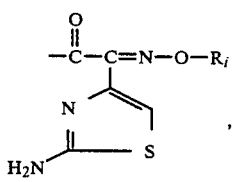

and $R_i$ is methyl, ethyl, carboxymethyl, 1-carboxy-1-methylethyl, 2,2,2-trifluoroethyl or 1-carboxycyclopropyl.

15. A 2-azetidinone in accordance with claim 12 wherein $R_1$ is

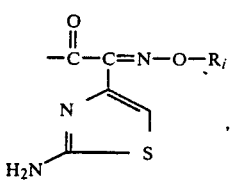

and $R_i$ is methyl, ethyl, carboxymethyl, 1-carboxy-1-methylethyl, 2,2,2-trifluoroethyl or 1-carboxycyclopropyl.

16. A 2-azetidinone in accordance with claim 3 wherein $R_1$ is

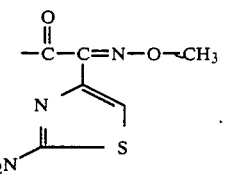

17. A 2-azetidinone in accordance with claim 12 wherein $R_1$ is

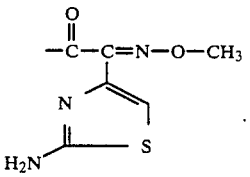

18. A compound in accordance with claim 3, [3S-[3[(Z),4β]]-[[3-[[(2-amino-4-thiazolyl methoxyimino)acetyl]amino]-4-methyl-2-oxo-1-azetidinyl]oxy]acetic acid, or an ester or pharmaceutically acceptable salt thereof.

19. A compound in accordance with claim 18, [3S-[3α(Z),4β]]-[[3-[[(2-amino-4-thiazolyl)-(methoxyimino)acetyl]amino]-4-methyl-2-oxo-1-aztidinyl]oxy]acetic acid, 1,1-dimethylethyl ester.

20. A compound in accordance with claim 18, [3S-[3α(Z),4β]]-[[3-[[(2-amino-4-thiazolyl)-(methoxyimino)acetyl]amino]4-methyl-2-oxo-1-azetidinyl]oxy]acetic acid, alkoxycarbonylalkyl ester.

21. A compound in accordance with claim 20, [3S-[3α(Z),4β]]-[[3-[[(2-amino-4-thiazolyl)-(methoxyimino)acetyl]amino]4-methyl-2-oxo-1-azetidinyl]oxy]acetic acid, ](3-pentyloxy)-carbonyl]methyl ester.

22. A compound in accordance with claim 20, [3S-[3α(Z),4β]]-[[3-[[(2-amino-4-thiazolyl)-(methoxyimino)acetyl]amino]4-methyl-2-oxo-1-azetidinyl]oxy]acetic acid, ](3-pentyloxy)-carbonyl]methyl ester.

23. A compound in accordance with claim 20, [3S-[3α(Z),4β]]-[[3-[[(2-amino-4-thiazolyl)-methoxyimino)acetyl]amino]-4-methyl-2-oxo-1-azetidinyl]oxy]acetic acid, [(4-heptyloxy)-carbonyl]methyl ester.

24. A β-lactam having the formula

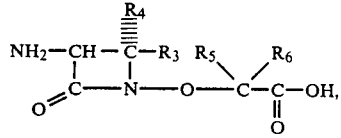

or an ester thereof, wherein $R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, —$CH_2X_1$, carboxyl, —S—$X_2$, —O—$X_2$,

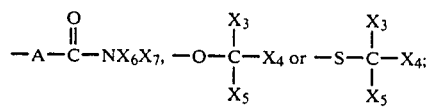

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

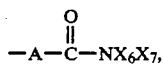

—S—$X_2$ or —O—$X_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —(CH$_2$)$_n$—, —CH$_2$—O—, —CH$_2$—NH— or —CH$_2$—S—CH$_2$; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle; and $R_5$ and $R_6$ are the same or different and each is hydrogen, alkyl, alkenyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle, or one of $R_5$ and $R_6$ is hydrogen and the other is azido, halomethyl, dihalomethyl, trihalomethyl, halogen, alkoxycarbonyl, alkenyl, alkynyl, 2-phenylethenyl, 2-phenylethynyl, carboxyl, —CH$_2$—$X_1$, —S—$X_2$, or

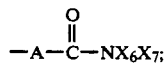

wherein the terms "alkyl" and "alkoxy" refer to groups having to 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "unsubstituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the term "unsubstituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (unsubstituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, t-trazolyl or one of the above groups substituted with one or more halogen, hydroxy, nitro, amino, cyano, trifluoromethyl, alkyl or 1 to 4 carbon atoms, alkoxy to 1 to 4 carbon atoms, alkylsulfonyl, phenyl, substituted phenyl, or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneimino, benzylideneimino or substituted alkyl, wherein the alkyl group has 1 to 4 carbon atoms, groups; and the term "substituted amino" refers to a group having the formula —N$Y_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino.

25. The compound in accordance with claim 3 having the formula